United States Patent
Tezapsidis et al.

(10) Patent No.: US 8,642,543 B2
(45) Date of Patent: *Feb. 4, 2014

(54) METHODS FOR TREATING PROGRESSIVE COGNITIVE DISORDERS RELATED TO NEUROFIBRILLARY TANGLES

(75) Inventors: Nikolaos Tezapsidis, West Orange, NJ (US); Steven Greco, Carlstadt, NJ (US); Mark Smith, Chagrin Falls, OH (US)

(73) Assignee: Neurotez, Inc., Bridgewater, NJ (US)

( * ) Notice: Subject to any disclaimer, the term of this patent is extended or adjusted under 35 U.S.C. 154(b) by 67 days.

This patent is subject to a terminal disclaimer.

(21) Appl. No.: 12/470,427

(22) Filed: May 21, 2009

(65) Prior Publication Data

US 2009/0291894 A1 Nov. 26, 2009
US 2012/0010132 A9 Jan. 12, 2012

Related U.S. Application Data

(63) Continuation-in-part of application No. 11/516,224, filed on Sep. 6, 2006, now Pat. No. 8,227,408.

(60) Provisional application No. 61/055,009, filed on May 21, 2008, provisional application No. 60/714,948, filed on Sep. 7, 2005.

(51) Int. Cl.
*A61K 38/22* (2006.01)

(52) U.S. Cl.
USPC .................. 514/5.8; 514/17.8; 514/18.2

(58) Field of Classification Search
None
See application file for complete search history.

(56) References Cited

U.S. PATENT DOCUMENTS

| | | | |
|---|---|---|---|
| 4,105,027 A | 8/1978 | Lundquist | |
| 4,192,309 A | 3/1980 | Poulsen | |
| 4,227,522 A | 10/1980 | Carris | |
| 4,627,432 A | 12/1986 | Newell et al. | |
| 4,778,054 A | 10/1988 | Newell et al. | |
| 4,811,731 A | 3/1989 | Newell et al. | |
| 5,035,237 A | 7/1991 | Newell et al. | |
| 5,521,283 A | 5/1996 | DiMarchi et al. | |
| 5,552,522 A | 9/1996 | DiMarchi et al. | |
| 5,552,523 A | 9/1996 | Basinki et al. | |
| 5,552,524 A | 9/1996 | Basinki et al. | |
| 5,698,389 A | 12/1997 | De la Brousse et al. | |
| 5,756,461 A | 5/1998 | Stephens | |
| 5,830,450 A | 11/1998 | Lallone | |
| 6,001,816 A | 12/1999 | Morsy et al. | |
| 6,001,968 A | 12/1999 | Friedman et al. | |
| 6,020,004 A | 2/2000 | Shah | |
| 6,025,324 A | 2/2000 | Bailon et al. | |
| 6,025,325 A | 2/2000 | Campfield et al. | |
| 6,048,837 A | 4/2000 | Friedman et al. | |
| 6,068,976 A | 5/2000 | Briggs et al. | |
| 6,284,221 B1 | 9/2001 | Schenk et al. | |
| 6,309,853 B1 | 10/2001 | Friedman et al. | |
| 6,352,970 B1 | 3/2002 | Ke et al. | |
| 6,429,290 B1 | 8/2002 | Friedman et al. | |
| 6,471,956 B1 | 10/2002 | Friedman et al. | |
| 6,475,984 B2 | 11/2002 | Kirwin et al. | |
| 6,518,235 B1 | 2/2003 | Oomura et al. | |
| 6,630,346 B1 | 10/2003 | Morsy et al. | |
| 6,716,810 B1 | 4/2004 | Brennan et al. | |
| 6,777,388 B1 | 8/2004 | Grasso et al. | |
| 6,921,527 B2 | 7/2005 | Platz et al. | |
| 6,936,439 B2 | 8/2005 | Mann et al. | |
| 7,074,397 B1 | 7/2006 | Matthews | |
| 7,109,159 B1 | 9/2006 | Barkan et al. | |
| 7,112,659 B2 | 9/2006 | Mann et al. | |
| 7,183,254 B2 | 2/2007 | DePaoli et al. | |
| 7,186,694 B2 | 3/2007 | Grasso et al. | |
| 7,208,572 B2 | 4/2007 | Grasso et al. | |
| 7,291,458 B2 | 11/2007 | Broekaert et al. | |
| 7,307,142 B2 | 12/2007 | Gertler et al. | |
| 7,354,896 B2 | 4/2008 | Kirwin et al. | |
| 7,407,929 B2 | 8/2008 | Gonzalez et al. | |
| 7,544,492 B1 | 6/2009 | Friedman et al. | |
| 7,582,292 B2 | 9/2009 | Wilkison et al. | |
| 7,612,043 B2 | 11/2009 | Gonzalez et al. | |
| 7,629,315 B2 | 12/2009 | Zhao | |
| 7,642,281 B2 | 1/2010 | Blackburn et al. | |
| 7,786,265 B2 | 8/2010 | Grasso et al. | |
| 7,790,683 B2 | 9/2010 | Grasso et al. | |
| 7,807,154 B2 | 10/2010 | Strasburger et al. | |
| 7,807,643 B2 | 10/2010 | Kirwin et al. | |
| 7,863,240 B2 | 1/2011 | Ilan et al. | |
| 8,227,408 B2 * | 7/2012 | Tezapsidis | 514/5.8 |
| 2002/0015709 A1 | 2/2002 | Kirwin et al. | |
| 2002/0019351 A1 | 2/2002 | Ke et al. | |

(Continued)

FOREIGN PATENT DOCUMENTS

WO 9116038 A1 10/1991
WO 9623513 A1 8/1996

(Continued)

OTHER PUBLICATIONS

Bor Luen Tang, 2008, Biochem. Biophys. Res. Comm., 368, pp. 181-185.*
Fewlass et al., 2004, FASEB, 18, pp. 1870-1878.*
Doherty et al., 2008, Neuroscience, 154, pp. 1297-1307.*
Zhang et al, 2007, Stroke, 38, pp. 2329-2336.*
Weng et al., 2007, J. Biol. Chem., 282, No. 47, pp. 34479-34491.*
Unger, R.H., "The Physiology of Cellular Liporegulation", Annu. Rev. Physiol., 2003, pp. 333-347, vol. 65, Annual Reviews.
Unger, R.H., "Lipotoxic Diseases", Annu. Rev. Med., 2002, pp. 319-336, vol. 53, Annual Reviews.
Ur, E. et al., "Leptin Immunoreactivity is Localized to Neurons in Rat Brain", Neuroendocrinology, 2002, pp. 264-272, vol. 75, S. Karger AG, Basel.
Vickers, J.C., "A Vaccine Against Alzheimer's Disease: Developments to Date", Drugs Aging, 2002, pp. 487-494, vol. 19, No. 7, Adis International Limited.

(Continued)

*Primary Examiner* — Olga N Chernyshev
(74) *Attorney, Agent, or Firm* — Lippincott Burnett LLP; Paul Burnett

(57) ABSTRACT

The described invention provides methods for treating or preventing progression of a progressive cognitive disease, disorder or condition, and methods for improving resilience of cognitive function in a subject in need thereof.

11 Claims, 4 Drawing Sheets

(56) References Cited

U.S. PATENT DOCUMENTS

| | | |
|---|---|---|
| 2002/0019352 A1 | 2/2002 | Brems et al. |
| 2002/0107211 A1 | 8/2002 | Friedman et al. |
| 2003/0036526 A1 | 2/2003 | Broekaert et al. |
| 2003/0130192 A1 | 7/2003 | Kirwin et al. |
| 2003/0215423 A1 | 11/2003 | Morsy et al. |
| 2004/0043932 A1 | 3/2004 | Grasso et al. |
| 2004/0053366 A1 | 3/2004 | Lo et al. |
| 2004/0202652 A1 | 10/2004 | Karsenty et al. |
| 2004/0213763 A1 | 10/2004 | Friedman et al. |
| 2005/0020496 A1 | 1/2005 | DePaoli et al. |
| 2005/0049193 A1 | 3/2005 | Grasso et al. |
| 2005/0065078 A1 | 3/2005 | Cawthorne et al. |
| 2005/0163799 A1 | 7/2005 | Mann et al. |
| 2005/0250690 A1 | 11/2005 | Gonzalez et al. |
| 2005/0272656 A1 | 12/2005 | Matthews |
| 2006/0079442 A1 | 4/2006 | Ilan et al. |
| 2006/0079443 A1 | 4/2006 | Ilan et al. |
| 2006/0154859 A1 | 7/2006 | Gertler et al. |
| 2006/0165683 A1 | 7/2006 | Karsenty et al. |
| 2006/0205660 A1 | 9/2006 | De Sauvage et al. |
| 2006/0206948 A1 | 9/2006 | Zhao |
| 2006/0281699 A1 | 12/2006 | Merchiers et al. |
| 2007/0066527 A1 | 3/2007 | Tezapsidis |
| 2007/0099836 A1 | 5/2007 | DePaoli et al. |
| 2007/0104697 A1 | 5/2007 | Wilkison et al. |
| 2007/0135510 A1 | 6/2007 | Blackburn et al. |
| 2007/0162987 A1 | 7/2007 | Grasso et al. |
| 2007/0218504 A1 | 9/2007 | Zhao |
| 2008/0009475 A1 | 1/2008 | Garner et al. |
| 2008/0108567 A1 | 5/2008 | Grasso et al. |
| 2008/0118503 A1 | 5/2008 | Strasburger et al. |
| 2008/0138811 A1 | 6/2008 | Mack et al. |
| 2008/0242612 A1 | 10/2008 | Kirwin et al. |
| 2009/0029919 A1 | 1/2009 | Gonzalez et al. |
| 2009/0031434 A1 | 1/2009 | Han |
| 2009/0175841 A1 | 7/2009 | Berry et al. |
| 2009/0281522 A1 | 11/2009 | Thio et al. |
| 2010/0113358 A1 | 5/2010 | Tezapsidis et al. |

FOREIGN PATENT DOCUMENTS

| | | |
|---|---|---|
| WO | 9623514 A1 | 8/1996 |
| WO | 9623515 A1 | 8/1996 |
| WO | 9623516 A1 | 8/1996 |
| WO | 9623517 A1 | 8/1996 |
| WO | 9623518 A1 | 8/1996 |
| WO | 9623519 A1 | 8/1996 |
| WO | 9623520 A1 | 8/1996 |
| WO | 9629405 A2 | 9/1996 |
| WO | 9724440 A1 | 7/1997 |
| WO | 9748419 A1 | 12/1997 |
| WO | 9748806 A1 | 12/1997 |
| WO | 9824896 A2 | 6/1998 |
| WO | 9846257 A1 | 10/1998 |
| WO | 9951253 A2 | 10/1999 |
| WO | 0009165 A1 | 2/2000 |
| WO | 0011173 A1 | 3/2000 |
| WO | 0020872 A1 | 4/2000 |
| WO | 0033658 A1 | 6/2000 |
| WO | 0040615 A2 | 7/2000 |
| WO | 0047741 A1 | 8/2000 |
| WO | 0076552 A1 | 12/2000 |
| WO | 0113935 A2 | 3/2001 |
| WO | 03020303 A1 | 3/2003 |
| WO | 03034996 A2 | 5/2003 |
| WO | 2005110461 A2 | 11/2005 |
| WO | 2005110468 A2 | 11/2005 |
| WO | 2006056987 A2 | 6/2006 |
| WO | 2006096816 A2 | 9/2006 |
| WO | 2008048691 A2 | 4/2008 |
| WO | 2008115880 A2 | 9/2008 |
| WO | 2008155403 A2 | 12/2008 |
| WO | 2009019427 A2 | 2/2009 |
| WO | 2009108340 A2 | 9/2009 |
| WO | 2009138762 A2 | 11/2009 |
| WO | 2010054017 A1 | 5/2010 |
| WO | 2009143380 A2 | 5/2011 |

OTHER PUBLICATIONS

Watson, G.S. et al. "The Role of Insulin Resistance in the Pathogenesis of Alzheimer's Disease: Implications for Treatment", CNS Drugs, 2003, pp. 27-45, vol. 17, No. 1, Adis International Limited.

Wilentz, R.E. et al., "Lipogenic Enzymes Fatty Acid Synthase and Acetyl-Coenzyme a Carboxylase are Coexpressed with Sterol Regulatory Element Binding Protein and Ki-67 in Fetal Tissues", Pediatr. Dev. Pathol., 2000, pp. 525-531, vol. 3, Society for Pediatric Pathology.

Wood, W.G. et al., "Brain Membrane Cholesterol Domains, Aging and Amyloid Beta-Peptides", Neurobiol. Aging, 2002, pp. 685-694, vol. 23, Elsevier Science, Inc.

Xiao, E. et al., "Leptin Modulates Inflammatory Cytokine and Neuroendocrine Responses to Endotoxin in the Primate", Endocrinology, Oct. 2003, pp. 4350-4353, vol. 144, No. 10, The Endocrine Society.

Yanagisawa, M. et al, "Role of Lipid Rafts in Integrin-Dependent Adhesion and gp130 Signalling Pathway in Mouse Embryonic Neural Precursor Cells", Genes Cells, 2004, pp. 801-809, vol. 9, Blackwell Publishing Limited.

Ye, F. et al., "The Dipeptide H-Trp-Glu-OH Shows Highly Antagonistic Activity Against PPARgamma: Bioassay with Molecular Modeling Simulation", Chembiochem, 2006, pp. 74-82, vol. 7, Wiley-VCH Verlag GmbH & Co. KGaA, Weinheim.

Yu, Y.-H. et al., "Posttrascriptional Control of the Expression and Function of Diacylglycerol Acyltransferase-1 in Mouse Adipocytes", J. Biol. Chem., Dec. 27, 2002, pp. 50876-50884, vol. 277, No. 52, The American Society for Biochemistry and Molecular Biology, Inc.

Zarkesh-Esfahani, H. et al., "High-Dose Leptin Activates Human Leukocytes Via Receptor Expression on Monocytes", J. Immunol., 2001, pp. 4593-4599, vol. 167, The American Association of Immunologists, Inc., Bethesda, MD.

Zhao, Y. et al., "Expression of Leptin Receptors and Response to Leptin Stimulation of Human Natural Killer Cell Lines", Biochem. Biophys. Res. Commun., 2003, pp. 247-252, vol. 300, Elsevier Science (USA), Academic Press.

Zhou, G. et al., "Role of AMP-Activated Protein Kinase in Mechanism of Metformin Action", J. Clin. Invest., Oct. 2001, pp. 1167-1174, vol. 108, No. 8, The American Society for Clinical Investigation.

Greco, S. J. et al., "Leptin reduces Alzheimer's disease-related tau phosphorylation in neuronal cells", Biochem. Biophys. Res. Commun., Nov. 21, 2008, vol. 376, No. 3, pp. 536-541.

Signore, A. P. et al., "Leptin neuroprotection in the CNS: mechanisms and therapeutic potentials.", J. Neurochem., Sep. 2008, vol. 106, No. 5, pp. 1977-1990.

American Psychiatric Association, "Diagnostic Criteria for Dementia of the Alzheimer's Type", Diagnostic and Statistical Manual of Mental Disorders, Fourth Edition, 1994, Copyright American Psychiatric Association.

Arnalich, F. et al., "Relationship of Plasma Leptin to Plasma Cytokines and Human Sepsis and Septic Shock", J. Infect. Dis., 1999, pp. 908-911, vol. 180, The Infectious Diseases Society of America.

Barrett-Connor, E. et al., "Weight Loss Precedes Dementia in Community-Dwelling Older Adults", J. Am. Geriatr. Soc., Oct. 1996, pp. 1147-1152, vol. 44, No. 10, Blackwell Publishing.

Batterham, R.L. et al., "Inhibition of Food Intake in Obese Subjects by Peptide YY3-36", N. Engl. J. Med., Sep. 4, 2003, pp. 941-948 vol. 349, No. 10, Massachusetts Medical Society.

Baumann, H. et al., "The Full-Length Leptin Receptor has Signaling Capabilities of Interleukin 6-Type Cytokine Receptors", Proc. Natl. Acad. Sci. USA, Aug. 1996, pp. 8374-8378, vol. 93, The National Academy of Sciences.

Benveniste, E.N. et al., "Immunological Aspects of Microglia: Relevance to Alzheimer's Disease", Neurochem. Int., 2001, pp. 381-391, vol. 39, Elsevier Science, Ltd.

Bickel, P.E. et al., "Flotillin and Epidermal Surface Antigen define a New Family of Caveolae-Associated Integral Membrane Proteins",

(56) References Cited

OTHER PUBLICATIONS

J. Biol. Chem., May 23, 1997, pp. 13793-137802, vol. 272, No. 21, The American Society for Biochemistry and Molecular Biology, Inc.
Bilancio, A. et al., "Key Role of the p110Delta Isoform of P13K in B-cell Antigen and IL-4 Receptor Signaling: Comparative Analysis of Genetic and Pharmacologic Interference with p110Delta Function in B Cells", Blood, 2006, pp. 642-650, vol. 107, No. 2, The American Society of Hematology, Washington DC.
Bjorbaek, C. et al., "The Role of SOCS-3 in Leptin Signaling and Leptin Resistance", J. Biol. Chem., Oct. 15, 1999, pp. 30059-30065, vol. 274, No. 42, The American Society for Biochemistry and Molecular Biology, Inc.
Blasko, I. et al., "TNFalpha Plus IFNgamma Induce the Production of Alzheimer Beta-Amyloid Peptides and Decrease the Secretion of APPs", FASEB J., Jan. 1999, pp. 63-68, vol. 13, The Federation of American Societies for Experimental Biology.
Bradford, M.M., "A Rapid and Sensitive Method for the Quantitation of Microgram Quantities of Protein Utilizing the Principle of Protein-Dye Binding", Anal. Biochem., May 7, 1976, pp. 248-254, vol. 72, No. 1-2, Elsevier B.V.
Brown, M.S. et al., "The SREBP Pathway: Regulation of Cholesterol Metabolism by Proteolysis of a Membrane-Bound Transcription Factor", Cell, May 2, 1997, pp. 331-340, vol. 89, Cell Press.
Caldefie-Chezet, F. et al., "Leptin: A Potential Regulator of Polymorphonuclear Neutrophil Bactericidal Action", J. Leukoc. Biol., Mar. 2001, pp. 414-418, vol. 69, The Society of Leukocyte Biology.
Carpino, L.A. et al., "The 9-Fluorenylmethoxycarbonyl Amino-Protecting Group", J. Org. Chem., 1972, pp. 3404-3409, vol. 37, American Chemical Society.
Chen, F. et al., "Characterization of ATP-Independent ERK Inhibitors Indentified Through Silico Analysis of the Active ERK2 Structure", Bioorg. Med. Chem. Lett., 2006, pp. 6281-6287, vol. 16, Elsevier, Ltd.
Cheng, A.N. et al., "Attenuation of Leptin Action and Regulation of Obesity by Protein Tyrosine Phosphatase 1B", Dev. Cell, Apr. 2002, pp. 497-503, vol. 2, Cell Press.
Chung, W.K. et al., "Heterozygosity for Lep/ob or Lepr/db Affects Body Composition and Leptin Homeostasis in Adult Mice", Am. J. Physiol. Regul. Integr. Comp. Physiol., 1998, pp. R985-R990, vol. 274, The American Physiological Society, Bethesda, MD.
Clare, P.M. et al., "The Cyclin-Dependent Kinases cdk2 and cdk5 Act by a Random, Anticooperative Kinetic Mechanism", J. Biol. Chem., Dec. 21, 2001, pp. 48292-48299, vol. 276, No. 51, The American Society for Biochemistry and Molecular Biology, Inc.
Conway, K.A. et al., "Fibrils Formed in Vitro from alpha-Synuclein and Two Mutant Forms Linked to Parkinson's Disease are Typical Amyloid", Biochemistry, 2000, pp. 2552-2563, vol. 39, American Chemical Society.
Cordy, J.M. et al., "Exclusively Targeting {beta}-Secretase to Lipid Rafts by GPI-Anchor Addition Up-regulates {beta}-Site Processing of the Amyloid Precursor Protein", Proc. Natl. Acad. Sci. USA., Sep. 30, 2003, pp. 11735-11740, vol. 100, The National Academy of Sciences.
Counce, M.E. et al., "Localization of Leptin Receptor in the Human Brain", Neuroendocrinology, Sep. 1997, pp. 145-150, vol. 66, S. Karger AG, Basel.
Danik, M. et al., "Brain Lipoprotein Metabolism and Its Relation to Neurodegenerative Disease", Crit. Rev. Neurobiol., 1999, pp. 357-407, vol. 13, No. 4, Begell House, Inc. Publishers.
De Laszlo, S.E. et al., "Pyrroles and Other Heterocycles as Inhibitors of P38 Kinase", Bioorg. Med. Chem. Lett., 1998, pp. 2689-2694, vol. 8, Elsevier B.V.
De Strooper, B., "Aph-1, Pen-2, and Nicastrin with Presenilin Generate an Active gamma-Secretase Complex", Neuron, Apr. 10, 2003, pp. 9-12, vol. 38, Cell Press.
Duff, K. et al., "Increased Amyloid-beta42(43) in Brains of Mice Expressing Mutant Presenilin 1", Nature, Oct. 1996, pp. 710-713, vol. 383, The Nature Publishing Group.
Emmerling, M.R. et al., "The Role of Complement in Alzheimer's Disease Pathology", Biochim. Biophys. Acta, 2000, pp. 158-171, vol. 1502, Elsevier B.V.
Fagan, A.M. et al., "Unique Lipoproteins Secreted by Primary Astrocytes from Wild Type, apoE(-/-), and Human apoE Transgenic Mice", J. Biol. Chem., Oct. 15, 1999, pp. 30001-30007, vol. 274, The American Society for Biochemistry and Molecular Biology.
Faggioni, R. et al., "Leptin Regulation of the Immune Response and the Immunodeficiency of Malnutrition", FASEB J., Dec. 2001, pp. 2565-2571, vol. 15, The Federation of American Societies for Experimental Biology.
Farr, S.A. et al., "Effects of Leptin on Memory Processing", Peptides, 2006, pp. 1420-1425, vol. 27, Elsevier, Inc.
Farris, W. et al., "Insulin-Degrading Enzyme Regulates the Levels of Insulin, Amyloid Beta-Protein, and the Beta-Amyloid Precursor Protein Intracellular Domain in vivo", Proc. Natl. Acad. Sci. USA., Apr. 1, 2003, pp. 4162-1467, vol. 100, The National Academy of Sciences.
Feng, B. et al., "The Endoplasmic Reticulum is the Site of Cholesterol-Induced Cytotoxicity in Macrophages", Nat. Cell Biol., 5:781-792 (2003).
Fewlass, D.C. et al., "Obesity-Related Leptin Regulates Alzheimer's Abeta", FASEB J., Dec. 2004, pp. 1870-1878, vol. 18, The Federation of American Societies for Experimental Biology.
Fields, G.B. et al., "Solid Phase Peptide Synthesis Utilizing 9-Fluorenylmethoxycarbonyl Amino Acids", Int. J. Pept. Protein Res., 1990, pp. 161-214, vol. 35, John Wiley & Sons, Inc.
Figueiredo-Pereira, M.E. et al., "Distinct Secretases, a Cysteine Protease and a Serine Protease, Generate the C Termini of Amyloid Beta-Proteins Abeta1-40 and Abeta1-42, respectively", J. Neurochem., 1999, pp. 1417-1422, vol. 72, Lippincott Williams & Wilkins, Inc., Philadelphia, International Society for Neurochemistry.
Ford, M.J. et al., "Selective Expression of Prion Protein in Peripheral Tissues of the Adult Mouse", Neuroscience, 2002, pp. 177-192, vol. 113, No. 1, Elsevier Science, Ltd.
Frenkel, D. et al., "Nasal Vaccination with a Proteasome-Based Adjuvant and Glatiramer Acetate Clears beta-Amyloid in a Mouse Model of Alzheimer Disease", J. Clin. Invest., Sep. 2005, pp. 2423-2433, vol. 115, No. 9, The American Society for Clinical Investigation.
Gandy, S. "The Role of Cerebral Amyloid beta Accumulation in Common Forms of Alzheimer Disease", J. Clin. Invest., May 2005, pp. 1121-1129, vol. 115, No. 5, The American Society for Clinical Investigation.
Ghosh, T.K. et al., "Transdermal and Topical Drug Delivery Systems", 2007, pp. 249-297, Culinary and Hospitality Industry Publications Services.
Han, Z. et al., "c-Jun N-Terminal Kinase is Required for Metalloproteinase Expression and Joint Destruction in Inflammatory Arthritis", J. Clin. Invest., Jul. 2001, pp. 73-81, vol. 108, No. 1, The American Society for Clinical Investigation.
Hardy, J. et al., "The Amyloid Hypothesis of Alzheimer's Disease: Progress and Problems on the Road to Therapeutics", Science, Jul. 19, 2002, pp. 353-356, vol. 297, American Association for the Advancement of Science.
Heshka, J.T. et al., "A Role for Dietary Fat in Leptin Receptor, OB-Rb Function", Life Sci., 2001, pp. 987-1003, vol. 69, Elsevier, Inc.
Holcomb, L. et al., "Accelerated Alzheimer-Type Phenotype in Transgenic Mice Carrying Both Mutant Amyloid Precursor Protein and Presenilin 1 Transgenes", Nat. Med. Jan. 1998, pp. 97-100, vol. 4, No. 1, Nature Publishing Group.
Hsiao, K. et al., "Correlative Memory Deficits, Abeta Elevation, and Amyloid Plaques in Transgenic Mice", Science, Oct. 4, 1996, pp. 99-102, vol. 274, American Association for the Advancement of Science.
Hu, Y. et al., "3-(Hydroxymethyl)-Bearing Phosphatidylinositol Ether Lipid Analogues and Carbonate Surrogates Block P13-K, Akt, and Cancer Cell Growth", J. Med. Chem., 2000, pp. 3045-3051, vol. 43, No. 16, American Chemical Society.
Idris, I. et al., "Familial Hyperinsulinaemia Associated with Epilepsy and Mental Retardation—A Syndrome of Familial Insulin Resistance", Diabet. Med., 2004, pp. 628-631, vol. 21, Diabetes, UK.
International Search Report for PCT/US09/63310 dated Feb. 25, 2010.

(56) References Cited

OTHER PUBLICATIONS

Ishida, A. et al., "Stabilization of Calmodulin-Dependent Protein Kinase II Through the Autoinhibitory Domain", J. Biol. Chem., Feb. 3, 1995, pp. 2163-2170, vol. 270, No. 5, The American Society for Biochemistry and Molecular Biology, Inc.

Isidori, A.M. et al., "Leptin and Aging: Correlation with Endocrine Changes in Male and Female Healthy Adult Populations of Different Body Weights", J. Clin. Endocrinol. Metab., 2000, pp. 1954-1962, vol. 85, No. 5, The Endocrine Society.

Johnsingh, A.A. et al., "Altered Binding of Mutated Presenilin with Cytoskeleton-Interacting Proteins", FEBS Lett., 2000, pp. 53-58, vol. 465, Elsevier B.V., Federation of European Biochemical Societies.

Kang, D.E. et al., "Modulation of Amyloid Beta-Protein Clearance and Alzheimer's Disease Susceptibility by the LDL Receptor-Related Protein Pathway", J. Clin. Invest., Nov. 2000, pp. 1159-1166, vol. 106, No. 9, The American Society for Clinical Investigation.

Han, B. S. et al., "A distinct death mechanism is induced by 1-methyl-4-phenylpyridinium or by 6-hydroxydopamine in cultured rat cortical neurons: degradation and dephosphorylation of tau,", Neurosci Lett., May 1, 2003, 341(2): 99-102.

Mesulam, M. M., "A plasticity-based theory of the pathogenesis of Alzheimer's disease," Ann N Y Acad Sci. 2000; 924:42-52.

Muma, N. A. et al., "6-hydroxydopamine-induced lesions of dopaminergic neurons alter the function of postsynaptic cholinergic neurons without changing cytoskeletal proteins," Exp Neurol., Mar. 2001;168(1): 135-43.

Torack, R. M. et al., "Hippocampal pyramidal cell response to 6-hydroxydopamine lesions of the rat ventral tegmental area," Brain Res. Mar. 6, 1992; 574(1-2):345-8.

Bancher, C. et al., "Accumulation of abnormally phosphorylated tau precedes the formation of neurofibrillary tangles in Alzheimer's disease," Brain Res. Jan. 16, 1989;477(1-2):90-9.

Greco, S. J. et al., "Leptin regulates tau phosphorylation and amyloid through AMPK in neuronal cells. Biochem Biophys Res Commun. Feb. 27, 2009;380(1):98-104.

De La Monte, S M & Wands, Jr "Review of insulin and insulin-like growth factor expression, signaling, and malfunction in the central nervous system: Relevance to Alzheimer's disease" Journal of Alzheimer's Disease 7 (2005) 45-61.

Kase, H. et al., "K-252 Compounds, Novel and Potent Inhibitors of Protein Kinase C and Cyclic Nucleotide-Dependent Protein Kinases", Biochem. Biophys. Res. Commun., Jan. 30, 1987, pp. 436-440, vol. 142, No. 2, Academic Press, Inc.

Kawarabayashi, T. et al., "Age-Dependent Changes in Brain, CSF, and Plasma Amyloid beta Protein in the Tg2576 Transgenic Mouse Model of Alzheimer's Disease", J. Neurosci., Jan. 15, 2001, pp. 372-381, vol. 21, No. 2, Society for Neuroscience.

Kawarabayashi, T. et al., "Dimeric Amyloid beta Protein Accumulates in Lipid Rafts Followed by Apolipoprotein E and Phosphorylated Tau Accumulattion in the Tg2576 Mouse Model of Alzheimer's Disease", J. Neurosci., Apr. 14, 2004, pp. 3801-3809, vol. 24, No. 15, Society for Neuroscience.

Kempen, H.J. et al., "Secretion of Apolipoproteins A-I and B by HepG2 Cells: Regulation by Substrates and Metabolic Inhibitors", J. Lipid Res., 1995, pp. 1796-1806, vol. 36, The American Society for Biochemistry and Molecular Biology, Inc.

Kersten, S. "Mechanisms of Nutritional and Hormonal Regulation of Lipogenesis", EMBO Rep., 2001, pp. 282-286, vol. 2, No. 41, European Molecular Biology Organization.

King, T.D. et al., "AMP-Activated Protein Kinase (AMPK) Activating Agents Cause Dephosphorylation of Akt and Glycogen Synthase Kinase-3", Biochem. Pharmacol., 2006, pp. 1637-1647, vol. 71, Elsevier B.V.

Klein, P.S. et al., "A Molecular Mechanism for the Effect of Lithium on Development", Proc. Natl. Acad. Sci. USA, Aug. 1996, pp. 8455-8459, vol. 93, The National Academy of Sciences.

Kotilinek, L.A. et al., "Reversible Memory Loss in a Mouse Transgenic Model of Alzheimer's Disease", J. Neurosci., Aug. 1, 2002, pp. 6331-6335, vol. 22, No. 15, Society for Neuroscience.

Ladu, M.J. et al., "Apolipoprotein E and Apolipoprotein E Receptors Modulate A Beta-Induced Glial Neuroinflammatory Responses", Neurochem. Int., 2001, pp. 427-434, vol. 39, Elsevier Science, Ltd.

Langer, R., "New Methods of Drug Delivery", Science, Sep. 28, 1990, pp. 1527-1533, vol. 249, American Association for the Advancement of Science.

Lee, Y. et al., "Liporegulation in Diet-Induced Obesity: The Antisteatotic Role of Hyperleptinemia", J. Biol. Chem., Feb. 23, 2001, pp. 5629-5635, vol. 276, No. 8, The American Society for Biochemistry and Molecular Biology, Inc.

Lemaire-Vieille, C. et al., "Epithelial and Endothelial Expression of the Green Fluorescent Protein Reporter Gene Under the Control of Bovine Prion Protein (PrP) Gene Regulatory Sequences in Transgenic Mice", Proc. Natl. Acad. Sci. USA., May 9, 2000, pp. 5422-5427, vol. 97, No. 10, The National Academy of Sciences.

Lichtenthaler, S.F. et al., "Amyloid at the Cutting Edge: Activation of Alpha-Secretase Prevents Amyloidogenesis in an Alzheimer Disease Mouse Model", J. Clin. Invest., May 2004, pp. 1384-1387, vol. 113, No. 10, The American Society for Clinical Investigation.

Loftus, T.M. et al., "Reduced Food Intake and Body Weight in Mice Treated with Fatty Acid Synthase Inhibitors", Science, Jun. 30, 2000, pp. 2379-2381, vol. 288, American Association for the Advancement of Science.

Lord, G.M. et al., "Leptin Modulates the T-Cell Immune Response and Reverses Starvation-Induced Immunosuppression", Nature, Aug. 27, 1998, pp. 897-901, vol. 394, Nature Publishing Group, Macmillan Publishers, Ltd.

Martin-Romero, C. et al., "Human Leptin Activates P13K and MAPK Pathways in Human Peripheral Blood Mononuclear Cells: Possible Role of Sam68", Cell. Immunol., 2001, pp. 83-91, vol. 212, Elsevier Science, Ltd.

Matarese, G. et al., "Leptin in Immunology", J. Immunol., 2005, pp. 3137-3142, vol. 174, The American Association of Immunologists, Inc.

Mazzali, G. et al., "Energy Balance in Alzheimer's Disease", J. Nutr. Health Aging, 2002, pp. 247-253, vol. 6, No. 4, Springer.

McGowen, D.P. et al., "Amyloid-like Inclusions in Huntington's Disease", Neuroscience, 2000, pp. 677-680, vol. 100, No. 4, Elsevier Science, Ltd, Great Britain.

Merrifield, R.B., "Solid Phase Peptide Synthesis. I. The Synthesis of a Tetrapeptide", J. Am. Chem. Soc., Jul. 20, 1963, pp. 2149-2154, vol. 85, American Chemical Society.

Minokoshi, Y. et al., "Leptin Stimulates Fatty-Acid Oxidation by Activating Amp-Activated Protein Kinase", Nature, Jan. 17, 2002, pp. 339-343, vol. 415, Macmillan Magazines, Ltd.

Mobbs, C.V. et al., "Block the FAS, Loose the Fat", Nat. Med., Apr. 2002, pp. 335-336, vol. 8, No. 4, Nature Publishing Group.

Narita, M. et al., "Cellular Catabolism of Lipid Poor Apolipoprotein E Via Cell Surface LDL Receptor-Related Protein", J. Biochem., pp. 743-749, vol. 132, No. 5, The Japanese Biochemical Society, 2002.

Peterson, T.A. et al., "Design, Development, Manufacturing, and Testing of Transdermal Drug Delivery Systems", Transdermal and Topical Drug Delivery Systems, 1997, pp. 249-297, Interpharm Press, Inc.

Postina, R. et al., "A Disintegrin-Metalloproteinase Prevents Amyloid Plaque Formation and Hippocampal Defects in an Alzheimer Disease Mouse Model", J. Clin. Invest., May 2004, pp. 1456-1464, vol. 113, No. 10, The American Society for Clinical Investigation.

Puglielli, L. et al., "Acyl-Coenzyme A: Cholesterol Acyltransferase Modulates the Generation of the Amyloid Beta-Peptide", Nat. Cell Biol., Oct. 2001, pp. 905-912, vol. 3, Macmillan Magazines Ltd.

Purves, D. et al., (Eds.) Neuroscience, 2001, Sinauer Associates, Inc., 2nd Edition, pp. 403, 554, 555 and 678.

Qiu, W.Q. et al., "Degradation of Amyloid Beta-Protein by a Metalloprotease Secreted by Microglia and other Neural and Non-neural Cells", J. Biol. Chem., Mar. 7, 1997, pp. 6641-6646, vol. 272, No. 10, The American Society for Biochemistry and Molecular Biology, Inc.

Refolo, L.M. et al., "Hypercholesterolemia Accelerates the Alzheimer's Amyloid Pathology in a Transgenic Mouse Model", Neurobiol. Dis., 2000, pp. 321-331, vol. 7, Academic Press.

(56) References Cited

OTHER PUBLICATIONS

Sanchez-Margelet, V. et al., "Human Leptin Signaling in Human Peripheral Blood Mononuclear Cells: Activation of the JAK-STAT Pathway", Cell. Immunol., 2001, pp. 30-36, vol. 211, Academic Press.

Schindler, C., "Transcriptional Responses to Polypeptide Ligands: The JAK-STAT Pathway", Ann. Rev. Biochem., 1995, pp. 621-651, vol. 64, Annual Reviews, Inc.

Schwartz, M.W. et al., "Central Nervous System Control of Food Intake", Nature, Apr. 6, 2000, pp. 661-671, vol. 404, MacMillan Magazines Ltd.

Shanley, L.J. et al., "Leptin Inhibits Rat Hippocampal Neurons Via Activation of Large Conductance Calcium-Activated K+ channels", Nat. Neurosci., Apr. 2002, pp. 299-300, vol. 5, No. 4, Nature Publishing Group.

Shimano, H. et al., "Isoform 1c of Sterol Regulatory Element Binding Protein is Less Active Than Isoform 1a in Livers of Transgenic Mice and in Cultured Cells", J. Clin. Invest., Mar. 1997, pp. 846-854, vol. 99, No. 5, The American Society for Clinical Investigation, Inc.

Shimoda, K. et al., "A High Percentage Yield of Tyrosine Hydroxylase-Positive Cells from Rat E14 Mesencephalic Cell Culture", Brain Res., Jul. 24, 1992, pp. 319-331, vol. 586, No. 2, Elsevier B.V.

Shimomura, I. et al., "Increased Levels of Nuclear SREBP-1c Associated with Fatty Livers in Two Mouse Models of Diabetes Mellitus", J. Biol. Chem., Oct. 15, 1999, pp. 30028-30032, vol. 274, No. 42, The American Society for Biochemistry and Molecular Biology, Inc.

Siddiquee, K. et al., "Selective Chemical Probe Inhibitor of Stat3, Identified Through Structure-Based Virtual Screening, Induces Antitumor Activity", Proc. Natl. Acad. Sci. USA, May 1, 2007, pp. 7391-7396, vol. 104, No. 18, The National Academy of Sciences.

Simons, M. et al., "Cholesterol Depletion Inhibits the Generation of Beta-Amyloid in Hippocampal Neurons", Proc. Natl. Acad. Sci. USA., May 1998, pp. 6460-6464, vol. 95, The National Academy of Sciences.

Sirtori, C.R. et al., "Re-evaluation of a Biguanide, Metformin: Mechanism of Action and Tolerability", Pharmacol. Res., 1994, pp. 187-228, vol. 30, No. 3, The Italian Pharmacological Society.

Sleeman, M.W. et al., "The Ciliary Neurotrophic Factor and its Receptor, CNTFR Alpha", Pharm. Acta Helv., 2000, pp. 265-272, vol. 74, Elsevier B.V.

Smith, J.L. et al., "Levadopa with Carbidopa Diminishes Glycogen Concentration, Glycogen Synthase Activity, and Insulin-Stimulated Glucose Transport in Rat Skeletal Muscle", J. Appl. Physiol., Dec. 2004, pp. 2339-2346, vol. 97, The American Physiological Society.

Takeshima, T. et al., "Standardized Methods to Bioassay Neurotrophic Factors for Dopaminergic Neurons", J. Neurosci. Methods, 1996, pp. 27-41, vol. 67, Elsevier B.V.

Takeshima, T. et al., "Mesencephalic Type 1 Astrocytes Rescue Dopaminergic Neurons from Death Induced by Serum Deprivation", J. Neurosci., Aug. 1994, pp. 4769-4779, vol. 14, The Society for Neuroscience.

Tartaglia, L.A., "The Leptin Receptor", J. Biol. Chem., Mar. 7, 1997, pp. 6093-6096, vol. 272, No. 10, The American Society for Biochemistry and Molecular Biology.

Tezapsidis, N. et al., "Microtubular Interactions of Presenilin Direct Kinesis of aBeta Peptide and its Precursors", FASEB J., Jul. 2003, pp. 1322-1324, vol. 17, The Federation of American Societies for Experimental Biology.

Tomas, E. et al., "Enhanced Muscle Fat oxidation and Glucose Transport by ACRP30 Globular Domain:acetyl-coA Carboxylase Inhibition and AMP-Activated Protein Kinase Activation", Proc. Natl. Acad. Sci. USA., Dec. 10, 2002, pp. 16309-16313, vol. 99, The National Academy of Sciences.

Toyoshima, Y. et al., "Leptin Improves Insulin Resistance and Hyperglycemia in a Mouse Model of Type 2 Diabetes", Endocrinology, Sep. 2005, pp. 4024-4035, vol. 146, No. 9, The Endocrine Society.

Truett, G.E. et al., "Rat Obesity Gene Fatty (fa) Maps to Chromosome 5: Evidence for Homology with the Mouse Gene Diabetes (db)", Proc. Natl. Acad. Sci., USA, Sep. 1991, pp. 7806-7809, vol. 88, The National Academy of Sciences.

Tschape, J.-A. et al., "Therapeutic Perspectives in Alzheimer's Disease", Recent Pat. CNS Drug Discov., 2006, pp. 119-127, vol. 1, No. 1, Bentham Science Publishers Ltd.

Ulery, P.G. et al., "LRP in Alzheimer's Disease: Friend or Foe?", J. Clin. Invest., Nov. 2000, pp. 1077-1079, vol. 106, No. 9, The American Society for Clinical Investigation.

\* cited by examiner

A.

B.

C.

D.

SEQUENCE LISTING

<160> NUMBER OF SEQ ID NOS: 6

<210> SEQ ID NO 1
<211> LENGTH: 770
<212> TYPE: PRT
<213> ORGANISM: Homo sapiens

<400> SEQUENCE: 1

```
Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
        115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Glu Ser Val Glu Glu Val Val Arg
        275                 280                 285

Glu Val Cys Ser Glu Gln Ala Glu Thr Gly Pro Cys Arg Ala Met Ile
    290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
                325                 330                 335

Cys Met Ala Val Cys Gly Ser Ala Met Ser Gln Ser Leu Leu Lys Thr
            340                 345                 350

Thr Gln Glu Pro Leu Ala Arg Asp Pro Val Lys Leu Pro Thr Thr Ala
        355                 360                 365
```

Ala Ser Thr Pro Asp Ala Val Asp Lys Tyr Leu Glu Thr Pro Gly Asp
370                 375                 380

Glu Asn Glu His Ala His Phe Gln Lys Ala Lys Glu Arg Leu Glu Ala
385                 390                 395                 400

Lys His Arg Glu Arg Met Ser Gln Val Met Arg Glu Trp Glu Glu Ala
                405                 410                 415

Glu Arg Gln Ala Lys Asn Leu Pro Lys Ala Asp Lys Lys Ala Val Ile
            420                 425                 430

Gln His Phe Gln Glu Lys Val Glu Ser Leu Glu Gln Glu Ala Ala Asn
        435                 440                 445

Glu Arg Gln Gln Leu Val Glu Thr His Met Ala Arg Val Glu Ala Met
450                 455                 460

Leu Asn Asp Arg Arg Arg Leu Ala Leu Glu Asn Tyr Ile Thr Ala Leu
465                 470                 475                 480

Gln Ala Val Pro Pro Arg Pro Arg His Val Phe Asn Met Leu Lys Lys
                485                 490                 495

Tyr Val Arg Ala Glu Gln Lys Asp Arg Gln His Thr Leu Lys His Phe
            500                 505                 510

Glu His Val Arg Met Val Asp Pro Lys Lys Ala Ala Gln Ile Arg Ser
        515                 520                 525

Gln Val Met Thr His Leu Arg Val Ile Tyr Glu Arg Met Asn Gln Ser
530                 535                 540

Leu Ser Leu Leu Tyr Asn Val Pro Ala Val Ala Glu Glu Ile Gln Asp
545                 550                 555                 560

Glu Val Asp Glu Leu Leu Gln Lys Glu Gln Asn Tyr Ser Asp Asp Val
                565                 570                 575

Leu Ala Asn Met Ile Ser Glu Pro Arg Ile Ser Tyr Gly Asn Asp Ala
            580                 585                 590

Leu Met Pro Ser Leu Thr Glu Thr Lys Thr Thr Val Glu Leu Leu Pro
        595                 600                 605

Val Asn Gly Glu Phe Ser Leu Asp Asp Leu Gln Pro Trp His Ser Phe
610                 615                 620

Gly Ala Asp Ser Val Pro Ala Asn Thr Glu Asn Glu Val Glu Pro Val
625                 630                 635                 640

Asp Ala Arg Pro Ala Ala Asp Arg Gly Leu Thr Thr Arg Pro Gly Ser
                645                 650                 655

Gly Leu Thr Asn Ile Lys Thr Glu Glu Ile Ser Glu Val Lys Met Asp
            660                 665                 670

Ala Glu Phe Arg His Asp Ser Gly Tyr Glu Val His His Gln Lys Leu
        675                 680                 685

Val Phe Phe Ala Glu Asp Val Gly Ser Asn Lys Gly Ala Ile Ile Gly
690                 695                 700

Leu Met Val Gly Gly Val Val Ile Ala Thr Val Ile Val Ile Thr Leu
705                 710                 715                 720

Val Met Leu Lys Lys Lys Gln Tyr Thr Ser Ile His His Gly Val Val
                725                 730                 735

Glu Val Asp Ala Ala Val Thr Pro Glu Glu Arg His Leu Ser Lys Met
            740                 745                 750

Gln Gln Asn Gly Tyr Glu Asn Pro Thr Tyr Lys Phe Phe Glu Gln Met
        755                 760                 765

Gln Asn
770

```
<210> SEQ ID NO 2
<211> LENGTH: 751
<212> TYPE: PRT
<213> ORGANISM: Homo sapiens

<400> SEQUENCE: 2

Met Leu Pro Gly Leu Ala Leu Leu Leu Leu Ala Ala Trp Thr Ala Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Arg Leu Asn Met His Met Asn Val Gln
        35                  40                  45

Asn Gly Lys Trp Asp Ser Asp Pro Ser Gly Thr Lys Thr Cys Ile Asp
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
            85                  90                  95

Trp Cys Lys Arg Gly Arg Lys Gln Cys Lys Thr His Pro His Phe Val
        100                 105                 110

Ile Pro Tyr Arg Cys Leu Val Gly Glu Phe Val Ser Asp Ala Leu Leu
    115                 120                 125

Val Pro Asp Lys Cys Lys Phe Leu His Gln Glu Arg Met Asp Val Cys
130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
            165                 170                 175

Asp Lys Phe Arg Gly Val Glu Phe Val Cys Cys Pro Leu Ala Glu Glu
        180                 185                 190

Ser Asp Asn Val Asp Ser Ala Asp Ala Glu Glu Asp Asp Ser Asp Val
    195                 200                 205

Trp Trp Gly Gly Ala Asp Thr Asp Tyr Ala Asp Gly Ser Glu Asp Lys
210                 215                 220

Val Val Glu Val Ala Glu Glu Glu Val Ala Glu Val Glu Glu Glu Glu
225                 230                 235                 240

Glu Ala Asp Asp Asp Glu Asp Asp Glu Asp Gly Asp Glu Val Glu Glu
            245                 250                 255

Glu Ala Glu Glu Pro Tyr Glu Glu Ala Thr Glu Arg Thr Thr Ser Ile
        260                 265                 270

Ala Thr Thr Thr Thr Thr Thr Thr Glu Ser Val Glu Glu Val Val Arg
    275                 280                 285

Glu Val Cys Ser Glu Gln Ala Glu Thr Gly Pro Cys Arg Ala Met Ile
290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
            325                 330                 335

Cys Met Ala Val Cys Gly Ser Ala Ile Pro Thr Thr Ala Ala Ser Thr
        340                 345                 350

Pro Asp Ala Val Asp Lys Tyr Leu Glu Thr Pro Gly Asp Glu Asn Glu
    355                 360                 365

His Ala His Phe Gln Lys Ala Lys Glu Arg Leu Glu Ala Lys His Arg
370                 375                 380

Glu Arg Met Ser Gln Val Met Arg Glu Trp Glu Glu Ala Glu Arg Gln
```

```
                385                 390                 395                 400
Ala Lys Asn Leu Pro Lys Ala Asp Lys Lys Ala Val Ile Gln His Phe
                    405                 410                 415

Gln Glu Lys Val Glu Ser Leu Glu Gln Glu Ala Ala Asn Glu Arg Gln
                420                 425                 430

Gln Leu Val Glu Thr His Met Ala Arg Val Glu Ala Met Leu Asn Asp
            435                 440                 445

Arg Arg Arg Leu Ala Leu Glu Asn Tyr Ile Thr Ala Leu Gln Ala Val
        450                 455                 460

Pro Pro Arg Pro Arg His Val Phe Asn Met Leu Lys Lys Tyr Val Arg
465                 470                 475                 480

Ala Glu Gln Lys Asp Arg Gln His Thr Leu Lys His Phe Glu His Val
                485                 490                 495

Arg Met Val Asp Pro Lys Lys Ala Ala Gln Ile Arg Ser Gln Val Met
                500                 505                 510

Thr His Leu Arg Val Ile Tyr Glu Arg Met Asn Gln Ser Leu Ser Leu
            515                 520                 525

Leu Tyr Asn Val Pro Ala Val Ala Glu Glu Ile Gln Asp Glu Val Asp
        530                 535                 540

Glu Leu Leu Gln Lys Glu Gln Asn Tyr Ser Asp Asp Val Leu Ala Asn
545                 550                 555                 560

Met Ile Ser Glu Pro Arg Ile Ser Tyr Gly Asn Asp Ala Leu Met Pro
                565                 570                 575

Ser Leu Thr Glu Thr Lys Thr Thr Val Glu Leu Leu Pro Val Asn Gly
                580                 585                 590

Glu Phe Ser Leu Asp Asp Leu Gln Pro Trp His Ser Phe Gly Ala Asp
            595                 600                 605

Ser Val Pro Ala Asn Thr Glu Asn Glu Val Glu Pro Val Asp Ala Arg
        610                 615                 620

Pro Ala Ala Asp Arg Gly Leu Thr Thr Arg Pro Gly Ser Gly Leu Thr
625                 630                 635                 640

Asn Ile Lys Thr Glu Glu Ile Ser Glu Val Lys Met Asp Ala Glu Phe
                645                 650                 655

Arg His Asp Ser Gly Tyr Glu Val His His Gln Lys Leu Val Phe Phe
                660                 665                 670

Ala Glu Asp Val Gly Ser Asn Lys Gly Ala Ile Ile Gly Leu Met Val
            675                 680                 685

Gly Gly Val Val Ile Ala Thr Val Ile Val Ile Thr Leu Val Met Leu
        690                 695                 700

Lys Lys Lys Gln Tyr Thr Ser Ile His His Gly Val Val Glu Val Asp
705                 710                 715                 720

Ala Ala Val Thr Pro Glu Glu Arg His Leu Ser Lys Met Gln Gln Asn
                725                 730                 735

Gly Tyr Glu Asn Pro Thr Tyr Lys Phe Phe Glu Gln Met Gln Asn
                740                 745                 750

<210> SEQ ID NO 3
<211> LENGTH: 695
<212> TYPE: PRT
<213> ORGANISM: Homo sapiens

<400> SEQUENCE: 3

Met Leu Pro Gly Leu Ala Leu Leu Leu Leu Ala Ala Trp Thr Ala Arg
1               5                   10                  15

Ala Leu Glu Val Pro Thr Asp Gly Asn Ala Gly Leu Leu Ala Glu Pro
```

```
                    20                  25                  30
Gln Ile Ala Met Phe Cys Gly Arg Leu Asn Met His Met Asn Val Gln
                35                  40                  45

Asn Gly Lys Trp Asp Ser Asp Pro Ser Gly Thr Lys Thr Cys Ile Asp
            50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
            100                 105                 110

Ile Pro Tyr Arg Cys Leu Val Gly Glu Phe Val Ser Asp Ala Leu Leu
            115                 120                 125

Val Pro Asp Lys Cys Lys Phe Leu His Gln Glu Arg Met Asp Val Cys
        130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Glu Val Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
            260                 265                 270

Ala Thr Thr Thr Thr Thr Thr Glu Ser Val Glu Glu Val Val Arg
            275                 280                 285

Val Pro Thr Thr Ala Ala Ser Thr Pro Asp Ala Val Asp Lys Tyr Leu
        290                 295                 300

Glu Thr Pro Gly Asp Glu Asn Glu His Ala His Phe Gln Lys Ala Lys
305                 310                 315                 320

Glu Arg Leu Glu Ala Lys His Arg Glu Arg Met Ser Gln Val Met Arg
                325                 330                 335

Glu Trp Glu Glu Ala Glu Arg Gln Ala Lys Asn Leu Pro Lys Ala Asp
            340                 345                 350

Lys Lys Ala Val Ile Gln His Phe Gln Glu Lys Val Glu Ser Leu Glu
        355                 360                 365

Gln Glu Ala Ala Asn Glu Arg Gln Gln Leu Val Glu Thr His Met Ala
    370                 375                 380

Arg Val Glu Ala Met Leu Asn Asp Arg Arg Arg Leu Ala Leu Glu Asn
385                 390                 395                 400

Tyr Ile Thr Ala Leu Gln Ala Val Pro Pro Arg Pro Arg His Val Phe
                405                 410                 415

Asn Met Leu Lys Lys Tyr Val Arg Ala Glu Gln Lys Asp Arg Gln His
            420                 425                 430

Thr Leu Lys His Phe Glu His Val Arg Met Val Asp Pro Lys Lys Ala
        435                 440                 445
```

```
Ala Gln Ile Arg Ser Gln Val Met Thr His Leu Arg Val Ile Tyr Glu
        450                 455                 460
Arg Met Asn Gln Ser Leu Ser Leu Leu Tyr Asn Val Pro Ala Val Ala
465                 470                 475                 480
Glu Glu Ile Gln Asp Glu Val Asp Glu Leu Leu Gln Lys Glu Gln Asn
                485                 490                 495
Tyr Ser Asp Asp Val Leu Ala Asn Met Ile Ser Glu Pro Arg Ile Ser
                500                 505                 510
Tyr Gly Asn Asp Ala Leu Met Pro Ser Leu Thr Glu Thr Lys Thr Thr
            515                 520                 525
Val Glu Leu Leu Pro Val Asn Gly Glu Phe Ser Leu Asp Asp Leu Gln
        530                 535                 540
Pro Trp His Ser Phe Gly Ala Asp Ser Val Pro Ala Asn Thr Glu Asn
545                 550                 555                 560
Glu Val Glu Pro Val Asp Ala Arg Pro Ala Ala Asp Arg Gly Leu Thr
                565                 570                 575
Thr Arg Pro Gly Ser Gly Leu Thr Asn Ile Lys Thr Glu Glu Ile Ser
                580                 585                 590
Glu Val Lys Met Asp Ala Glu Phe Arg His Asp Ser Gly Tyr Glu Val
            595                 600                 605
His His Gln Lys Leu Val Phe Phe Ala Glu Asp Val Gly Ser Asn Lys
        610                 615                 620
Gly Ala Ile Ile Gly Leu Met Val Gly Gly Val Val Ile Ala Thr Val
625                 630                 635                 640
Ile Val Ile Thr Leu Val Met Leu Lys Lys Lys Gln Tyr Thr Ser Ile
                645                 650                 655
His His Gly Val Val Glu Val Asp Ala Ala Val Thr Pro Glu Glu Arg
            660                 665                 670
His Leu Ser Lys Met Gln Gln Asn Gly Tyr Glu Asn Pro Thr Tyr Lys
        675                 680                 685
Phe Phe Glu Gln Met Gln Asn
    690                 695

<210> SEQ ID NO 4
<211> LENGTH: 39
<212> TYPE: PRT
<213> ORGANISM: Homo sapiens

<400> SEQUENCE: 4

Asp Ala Glu Phe Arg His Asp Ser Gly Tyr Glu Val His His Gln Lys
1               5                   10                  15
Leu Val Phe Phe Ala Glu Asp Val Gly Ser Asn Lys Gly Ala Asn Gly
                20                  25                  30
Leu Met Val Gly Gly Val Val
        35

<210> SEQ ID NO 5
<211> LENGTH: 41
<212> TYPE: PRT
<213> ORGANISM: Homo sapiens

<400> SEQUENCE: 5

Asp Ala Glu Phe Arg His Asp Ser Gly Tyr Glu Val His His Gln Lys
1               5                   10                  15
Leu Val Phe Phe Ala Glu Asp Val Gly Ser Asn Lys Gly Ala Asn Gly
                20                  25                  30
Leu Met Val Gly Gly Val Val Ile Ala
```

```
                  35                  40

<210> SEQ ID NO 6
<211> LENGTH: 42
<212> TYPE: PRT
<213> ORGANISM: Homo sapiens

<400> SEQUENCE: 6

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Asn Gly
            20                  25                  30

Leu Met Val Gly Gly Val Val Ile Ala Thr
            35                  40
```

METHODS FOR TREATING PROGRESSIVE COGNITIVE DISORDERS RELATED TO NEUROFIBRILLARY TANGLES

CROSS REFERENCES

This application claims the benefit of priority of U.S. application 61/055,009, filed May 21, 2008, which is incorporated by reference in its entirety. This application is also a continuation-in-part of U.S. application Ser. No. 11/516,224 (filed Sep. 6, 2006), which claims the benefit of priority from U.S. Provisional Application No. 60/714,948 (filed Sep. 7, 2005).

STATEMENT OF GOVERNMENT FUNDING

This invention was made with government support under Grant Number SBIR—1R43AG029670 awarded by the National Institute on Aging. The government has certain rights in the invention.

FIELD OF THE INVENTION

The described invention relates to methods for treating a progressive cognitive disorder and methods for improving resilience of cognitive function.

BACKGROUND OF THE INVENTION

Alzheimer's Disease

Alzheimer's disease (also called "AD", "senile dementia of the Alzheimer Type (SDAT)" or "Alzheimer's") is a neurodegenerative disorder of the central nervous system ("CNS"). AD is usually diagnosed clinically from the patient history, collateral history from relatives, and clinical observations, based on the presence of characteristic neurological and neuropsychological features.

AD is characterized by loss of neurons and synapses in the cerebral cortex and certain subcortical regions. This loss results in gross atrophy of the affected regions, including degeneration in the temporal lobe and parietal lobe, and parts of the frontal cortex and cingulate gyrus. Both amyloid plaques ("AP") and neurofibrillary tangles ("NFT") are clearly visible by microscopy in brains of those afflicted with AD. Plaques are dense, mostly insoluble deposits of amyloid-beta ("Aβ") protein and cellular material outside and around neurons. NFT are aggregates of the microtubule-associated protein "tau", which have become hyperphosphorylated and accumulate inside the cells themselves. Although many older individuals develop some plaques and tangles as a consequence of ageing, the brains of AD patients have a greater number of such plaques and tangles in specific brain regions, such as the temporal lobe.

AD is characterized histologically by the presence of extracellular amyloid deposits in the brain, together with widespread neuronal loss. Extracellular amyloid deposits are known as neuritic or senile plaques. Amyloid deposits also may be found within and around blood vessels. The main protein constituent of AD and AD-like senile plaques is Aβ. Aβ may be detected in plasma and cerebrospinal fluid ("CSF") in vivo, and in cell culture media in vitro.

The terms "amyloid peptide" "amyloid β peptide" and "Aβ" are used interchangeably herein to refer to the family of peptides generated through proteolytic processing of the amyloid precursor protein (APP).

APP exists as three different spliced isoforms, one having 770 amino acids (isoform a) (SEQ ID NO:1), one having 751 amino acids (isoform b) (SEQ ID NO:2), and one having 695 amino acids (SEQ ID NO:3). The term "APP" as used herein refers to all three isoforms. The terms "amyloid peptide" "amyloid β peptide" and "Aβ" include, but are not limited to, Aβ40 (SEQ ID NO:4), Aβ42 (SEQ ID NO:5) and Aβ43 (SEQ ID NO:6). The two major forms of Aβ are Aβ40 (SEQ ID NO:4), corresponding to a 40 amino acid-long peptide and Aβ42 (SEQ ID NO:5), corresponding to a 42 amino acid-long peptide. Aβ43 (SEQ ID NO:6) corresponds to a 43 amino acid-long Aβ peptide.

It generally is believed that brain lipids are intricately involved in Aβ-related pathogenic pathways. The Aβ peptide is the major proteinaceous component of the amyloid plaques found in the brains of AD patients and is regarded by many as the culprit of the disorder. The amount of extracellular Aβ accrued is critical for the pathobiology of AD and depends on the antagonizing rates of its production/secretion and its clearance. Studies have shown that neurons depend on the interaction between Presenilin 1 ("PS1") and Cytoplasmic-Linker Protein 170 ("CLIP-170") to both generate Aβ and to take it up through the lipoprotein receptor related protein ("LRP") pathway. Further to this requirement, formation of Aβ depends on the assembly of key proteins in lipid rafts ("LRs"). The term "lipid rafts" as used herein refers to membrane microdomains enriched in cholesterol, glycosphingolipids and glucosylphosphatidyl-inositol-(GPI)-tagged proteins implicated in signal transduction, protein trafficking and proteolysis. Within the LRs it is believed that Aβ's precursor, Amyloid Precursor Protein ("APP"), a type I membrane protein, is cleaved first by the protease β-secretase (BACE) to generate the C-terminal intermediate fragment of APP, CAPPβ, which remains embedded in the membrane. CAPPβ subsequently is cleaved at a site residing within the lipid bilayer by γ-secretase, a high molecular weight multiprotein complex containing presenilin, (PS1/PS2), nicastrin, PEN-2, and APH-1 or fragments thereof. Aβ finally is released outside the cell, where it may: i) start accumulating following oligomerization and exerting toxicity to neurons, or ii) be removed either by mechanisms of endocytosis (involving apolipoprotein-E (apoE) and LRP or Scavenger Receptors) or by degradation by extracellular proteases including insulin-degrading enzyme (IDE) and neprilysin.

It generally is believed that soluble Aβ oligomers, prior to plaque buildup, exert neurotoxic effects leading to neurodegeneration, synaptic loss and dementia. Further, increased Aβ levels may result from abnormal lipid accumulation, thereby producing altered membrane fluidity and lipid raft composition.

The presence of NFT is a characteristic of AD brains. These aggregations of hyperphosphorylated tau protein also are referred to as "Paired Helical filaments" (PHF). The role of PHF, whether as a primary causative factor in AD or in a more peripheral role, is uncertain. However, the accumulation of PHF cause the destabilization of the microtubule network, thus compromising neuronal scaffolding and disrupting cellular trafficking and signal transduction/communication, and leading to neuronal death.

NFT are not specific to AD; NFT also are seen in Creutzfeldt-Jakob disease, Supranuclear Palsy, corticobasal neurodegeneration and Frontaltemporal Dementia with Parkinsonism linked to chromosome 17 (FTDP-17). This suggests that NFT may represent endpoints leading to neurodegeneration, which may be generated by a number of causative events/insults.

Leptin

Leptin is a helical protein secreted by adipose tissue, which acts on a receptor site in the ventromedial nucleus of the hypothalamus to curb appetite and increase energy expenditure as body fat stores increase. Leptin levels are 40% higher in women, and show a further 50% rise just before menarche, later returning to baseline levels. Leptin levels are lowered by fasting and increased by inflammation.

Human genes encoding both leptin and the leptin receptor site have been identified. Laboratory mice having mutations on the ob gene, which encodes leptin, become morbidly obese, diabetic, and infertile; administration of leptin to these mice improves glucose tolerance, increases physical activity, reduces body weight by 30%, and restores fertility. Mice with mutations of the db gene, which encodes the leptin receptor, also become obese and diabetic but do not improve with administration of leptin. Although mutations in both the leptin and leptin receptor genes have been found in a small number of morbidly obese human subjects with abnormal eating behavior, the majority of obese persons do not show such mutations, and have normal or elevated circulating levels of leptin. The immune deficiency seen in starvation may result from diminished leptin secretion. Mice lacking the gene for leptin or its receptor show impairment of T-cell function, and, in laboratory studies, leptin has induced a proliferative response in human CD4 lymphocytes.

Leptin also controls insulin sensitivity. Within the CNS, leptin crosses the blood brain barrier to bind specific receptors in the brain to mediate food intake, body weight and energy expenditure. In general, (i) leptin circulates at levels proportional to body fat; (ii) leptin enters the CNS in proportion to its plasma concentration; (iii) leptin receptors are found in brain neurons involved in regulating energy intake and expenditure; and (iv) leptin controls food intake and energy expenditure by acting on receptors in the mediobasal hypothalmus.

It generally is believed that leptin inhibits the activity of neurons that contain neuropeptide Y (NPY) and agouti-related peptide (AgRP), and increases the activity of neurons expressing α-melanocyte-stimulating hormone (α-MSH). The NPY neurons are a key element in the regulation of appetite; small doses of NPY injected into the brains of experimental animals stimulates feeding, while selective destruction of the NPY neurons in mice causes them to become anorexic. Conversely, α-MSH is an important mediator of satiety, and differences in the gene for the receptor at which α-MSH acts in the brain are linked to obesity in humans.

It is not known how disturbances of production and aggregation of Aβ peptide give rise to the pathology of AD or other progressive cognitive disorders. There remains a need for clinical therapy and diagnostic methods of progressive cognitive disorders related to accumulation of neurofibrillary tangles.

Figure 1:
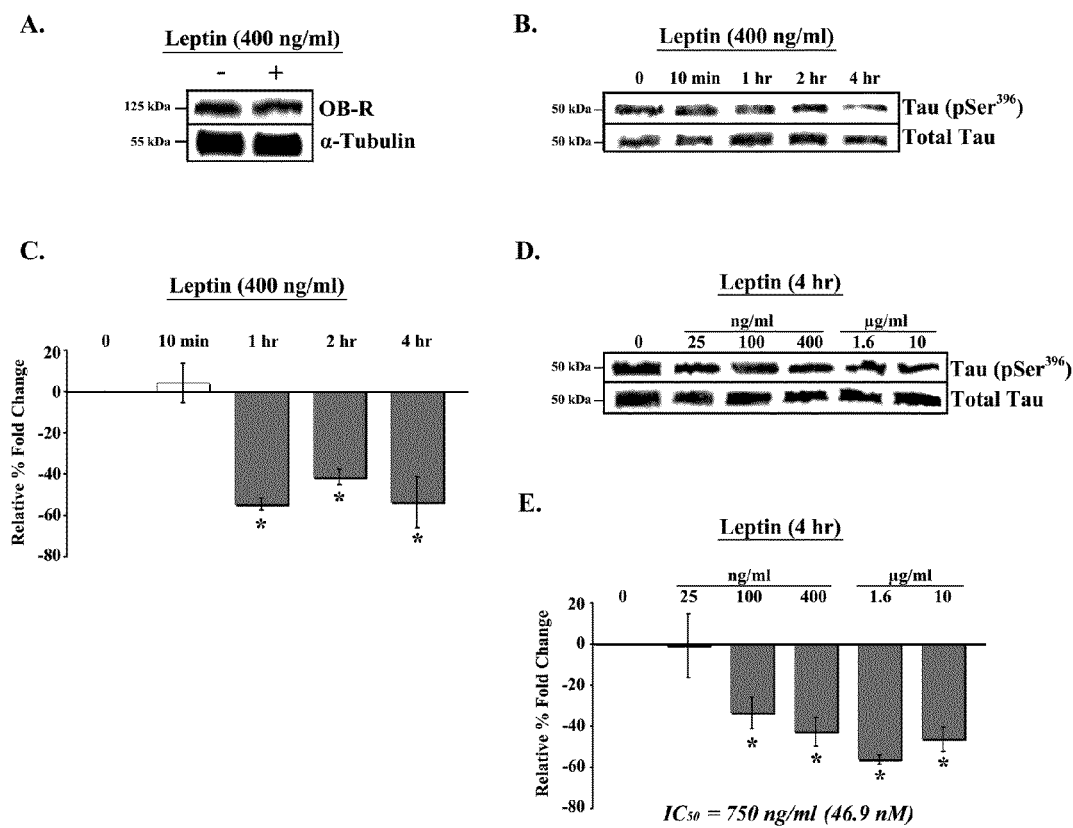
FIG. 1 shows time- and dose-dependent dephosphorylation of tau by leptin in RA-SY5Y. Human neuroblastoma cells of the SY5Y cell line were induced for 7 days with retinoic acid (RA) (10 μM) to promote neuronal differentiation (RA-SY5Y). A. Induced cells were treated with leptin (400 ng/ml) for 4 hrs, or non-treated (placebo). Whole cell extracts were prepared and analyzed by western blot with anti-OB-R (leptin receptor). Membranes were stripped and re-probed with anti-α-tubulin for normalization. Representative blot is shown, n=3. B. Whole cell extracts from cells treated for various times with leptin (400 ng/ml), or placebo, were prepared and analyzed by western blot with anti-tau (pSer$^{396}$). Membranes were stripped and re-probed with anti-tau (total) for normalization. Representative blot is shown, n=3. C. Normalized band densities from B were analyzed by densitometry. Results are presented as the mean±SD percent fold change, relative to placebo-treated samples, which were arbitrarily assigned a value of 0. D. Induced cells were treated with various concentrations of leptin for 4 hrs, or placebo. Experiments were then preformed as in B. E. Normalized band densities from D were analyzed as in C. $IC_{50}$ represents the leptin concentration at which tau (pSer$^{396}$) phosphorylation is decreased by 50 percent. *p<0.05 vs. non-treated.

Normalized band densities from D were analyzed as in C. $IC_{50}$ represents the AICAR concentration at which tau ($pSer^{396}$) phosphorylation is decreased by 50 percent. *$p<0.05$ vs. non-treated.

SUMMARY

According to one aspect, the described invention provides a method for treating a progressive cognitive disorder, the method comprising the step of: (a) administering to a subject in need thereof a first composition comprising (i) a phosphorylated tau accumulation-modulating amount of a leptin composition, or a pharmaceutically acceptable salt thereof, and (ii) a pharmaceutically acceptable carrier, and (b) modulating accumulation of phosphorylated tau in cerebrospinal fluid of the subject. According to one embodiment of the method, the progressive cognitive disorder is selected from the group consisting of Alzheimer's Disease, progressive supranuclear palsy, dementia, dementia pugilistica, Creutzfeldt-Jakob disease, frontotemporal dementia, Pick's disease, and FTDP-17 (parkinsonism) corticobasal degeneration. According to another embodiment, the leptin composition is a leptin, or a pharmaceutically acceptable salt thereof. According to another embodiment, the leptin composition is a leptin mimic, or a pharmaceutically acceptable salt thereof. According to another embodiment, the leptin composition is a leptin derivative, or a pharmaceutically acceptable salt thereof. According to another embodiment, the leptin composition is a leptin agonist, or a pharmaceutically acceptable salt thereof. According to another embodiment, the phosphorylated tau accumulation-modulating amount is an amount from about 0.01 mg/kg body weight to about 100 mg/kg body weight. According to another embodiment, the first composition further comprises a second therapeutic agent. According to another embodiment, the second therapeutic agent is at least one of an antibiotic, an anti-fungal agent, an antiviral agent, an anti-protozoal agent, a steroidal anti-inflammatory agent, a non-steroidal anti-inflammatory agent, an anti-oxidant; a hormone; a vitamin; an antihistamine agent, and a chemotherapeutic agent. According to another embodiment, the progressive disorder comprises accumulation of neurofibrillary tangles in brain.

According to another aspect, the described invention provides a method for improving resilience of cognitive function in a subject in need thereof, the method comprising the steps of (a) administering to the subject a composition comprising (i) a cognitive function-enhancing amount of a leptin composition, and (ii) a pharmaceutically acceptable carrier; and (b) modulating accumulation of phosphorylated tau in cerebrospinal fluid of the subject. According to one embodiment of the method, the leptin composition comprises at least one of a leptin, a leptin mimic, a leptin derivative, an AMP-dependent protein kinase activator, a leptin agonist, a leptin blocker, a mimic of a leptin blocker, a leptin antagonist, an AMP-dependent protein kinase inhibitor; or pharmaceutically acceptable salts thereof. According to another embodiment, the leptin composition further comprises a second therapeutic agent. According to another embodiment, the second therapeutic agent is at least one of an antibiotic, an anti-fungal agent, an antiviral agent, an anti-protozoal agent, a steroidal anti-inflammatory agent, a non-steroidal anti-inflammatory agent, an anti-oxidant; a hormone; a vitamin; an antihistamine agent, and a chemotherapeutic agent.

DETAILED DESCRIPTION OF THE INVENTION

The described invention relates to methods for treating or preventing a progressive cognitive disorder and methods for improving resilience of cognitive function.

According to one aspect, the described invention provides a method for treating a progressive cognitive disorder, the method comprising the steps of: (a) administering to a subject in need thereof a first composition comprising (i) a phosphorylated tau accumulation-modulating amount of a leptin composition, and (ii) a pharmaceutically acceptable carrier, and (b) modulating accumulation of phosphorylated tau. in cerebrospinal fluid of the subject.

According to another aspect, the described invention provides a method for preventing progression of a progressive cognitive disorder, the method comprising the steps of (a) administering to a subject in need thereof a first composition comprising (i) a phosphorylated tau accumulation-modulating amount of a leptin composition, and (ii) a pharmaceutically acceptable carrier, and (b) modulating accumulation of phosphorylated tau in cerebrospinal fluid of the subject.

According to one embodiment, the leptin composition comprises a leptin, or a pharmaceutically acceptable salt thereof. According to another embodiment, the leptin composition comprises a leptin mimic, or a pharmaceutically acceptable salt thereof. According to another embodiment, the leptin composition comprises a leptin derivative, or a pharmaceutically acceptable salt thereof. According to another embodiment, the leptin composition comprises a leptin agonist, or a pharmaceutically acceptable salt thereof. According to another embodiment, the leptin composition comprises an AMP-dependent protein kinase activator, or a pharmaceutically acceptable salt thereof. According to another embodiment, the leptin composition comprises a mimic of a leptin blocker, or a pharmaceutically acceptable salt thereof. According to another embodiment, the leptin composition comprises a leptin antagonist, or a pharmaceutically acceptable salt thereof. According to another embodiment, the leptin composition comprises an AMP-dependent protein kinase inhibitor, or a pharmaceutically acceptable salt thereof.

According to another embodiment, the leptin composition comprises at least one of a leptin, a leptin mimic, a leptin derivative, a leptin agonist, an AMP-dependent protein kinase activator, a mimic of a leptin blocker, a leptin antagonist, an AMP-dependent protein kinase inhibitor, or pharmaceutically acceptable salts thereof.

The term "treat" or "treating" as used herein refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously symptomatic for the disorder(s).

The term "reduce" or "reducing" as used herein refers to limit occurrence of the disorder in individuals at risk of developing the disorder.

The term "modulate" as used herein means to regulate, alter, adapt, or adjust to a certain measure or proportion.

The term "disease" or "disorder" as used herein refers to an impairment of health or a condition of abnormal functioning. The term "syndrome," as used herein, refers to a pattern of symptoms indicative of some disease or condition. The term "injury," as used herein, refers to damage or harm to a structure or function of the body caused by an outside agent or force, which may be physical or chemical. The term "condition", as used herein, refers to a variety of health states and is meant to include disorders or diseases caused by any underlying mechanism or disorder, injury, and the promotion of healthy tissues and organs.

Progressive cognitive disorders include, but are not limited to, progressive supranuclear palsy; dementia; dementia pugilistica; AD; Creutzfeldt-Jakob disease; frontotemporal dementia; Pick's disease; other tau-positive pathology including FTDP-17 (parkinsonism) corticobasal degeneration; frontotemporal lobar degeneration (FTLD); dementia lacking distinctive histology.

The term "administering" as used herein refers to causing to take or apportioning and includes in vivo administration, as well as administration directly to tissue ex vivo. Generally, compositions may be administered systemically either orally, buccally, parenterally, topically, by inhalation or insufflation (i.e., through the mouth or through the nose), or rectally in dosage unit formulations containing conventional nontoxic pharmaceutically acceptable carriers, adjuvants, and vehicles as desired, or may be locally administered by means such as, but not limited to, injection, implantation, grafting, topical application, or parenterally.

The terms "subject" or "individual" or "patient" are used interchangeably to refer to a member of an animal species of mammalian origin, including humans.

The phrase "a subject having a progressive cognitive disease" as used herein refers to a subject who presents with diagnostic markers and/or symptoms associated with a progressive cognitive disease. A progressive cognitive disease is usually diagnosed clinically from the patient history, collateral history from relatives, and clinical observations, based on the presence of characteristic neurological and neuropsychological features and the absence of alternative conditions. These criteria require that the presence of cognitive impairment, and a suspected dementia syndrome, be confirmed by neuropsychological testing. Advanced medical imaging with computed tomography (CT) or magnetic resonance imaging (MRI), and with single photon emission computed tomography (SPECT) or positron emission tomography (PET) may be used to help exclude other cerebral pathology or subtypes of dementia. Assessment of intellectual functioning including memory testing can further characterize the state of the disease. A histopathologic confirmation including a microscopic examination of brain tissue may be required for a definitive diagnosis. For AD, eight cognitive domains are most commonly impaired: memory, language, perceptual skills, attention, constructive abilities, orientation, problem solving and functional abilities. These domains are equivalent to the NINCDS-ADRDA Alzheimer's Criteria as listed in the *Diagnostic and Statistical Manual of Mental Disorders* (DSM-IV-TR) published by the American Psychiatric Association (incorporated in its entirety herein by reference).

A subject at risk of having a progressive cognitive disease is one who has one or more predisposing factors to the development of a progressive cognitive disease.

A subject in need thereof is a patient having, or at risk of having, a progressive cognitive disease.

The term "dementia" as used herein refers to a decline or a progressive decline in cognitive function due to damage or disease in the brain beyond what might be expected from normal aging. The term "cognitive function" refers to the intellectual processes resulting in an understanding, perception, or awareness of one's ideas as well as the ability to perform mental tasks, such as thinking, learning, judging, remembering, computing, controlling motor functions, and the like.

The term "peptidomimetic" refers to a small protein-like chain designed to mimic or imitate a peptide. A peptidomimetic may comprise non-peptidic structural elements capable of mimicking (meaning imitating) or antagonizing (meaning neutralizing or counteracting) the biological action(s) of a natural parent peptide. The terms "leptin peptidomimetic" "leptin mimic", and "leptin mimetic" are used interchangeably herein to refer to a leptin derivative comprising a functional domain of a leptin protein that produces a biological effect. In chemistry, a derivative is a compound that at least theoretically may be formed from a precursor compound. These derivatives may be combined with another molecule to produce or enhance the biological effect. The biological effect may include, for example, but is not limited to, modulating amyloid peptide levels within a subject; modulating tau phosphorylation levels within a subject; decreasing amyloid peptide levels within a subject; decreasing tau phosphorylation levels within a subject, and the like.

The term "antagonist" as used herein refers to a substance that counteracts the effects of another substance. The term "agonist" as used herein refers to a chemical substance capable of activating a receptor to induce a full or partial pharmacological response. The term "blocker" as used herein refers to a substance that inhibits the physiological action of another substance.

The term "leptin agonist" refers to a compound capable of activating the leptin receptor and/or downstream effectors and of modulating amyloid peptide levels or tau phosphorylation in a subject. Such effectors may include, for example, but are not limited to, AMP-dependent protein kinase ("AMPK") and sterol regulatory element binding proteins ("SREBP").

The leptin receptor (OB-R), a member of the class I cytokine receptor superfamily, has at least six isoforms as a result of alternative splicing. As used herein the term "isoform" refers to a version of a protein that has the same function as another protein but that has some small difference(s) in its sequence. All isoforms of OB-R share an identical extracellular ligand-binding domain. Leptin's functional receptor (OB-Rb), the b isoform, is expressed not only in the hypothalamus, where it regulates energy homeostasis and neuroendocrine function, but also in other brain regions and in the periphery, including all cell types of innate and adaptive immunity. The full-length b isoform (OB-Rb) lacks intrinsic tyrosine kinase activity and is involved in several downstream signal transduction pathways.

The terms "therapeutically effective amount", an "amount effective", or "pharmaceutically effective amount" of one or more of the active agents are used interchangeably to refer to an amount that is sufficient to provide the intended benefit of treatment. An effective amount of the active agents that can be employed according to the described invention generally ranges from generally about 0.01 mg/kg body weight to about 100 g/kg body weight. However, dosage levels are based on a variety of factors, including the type of injury, the age, weight, sex, medical condition of the patient, the severity of the condition, the route of administration, and the particular active agent employed. Thus the dosage regimen may vary widely, but can be determined routinely by a physician using standard methods. Additionally, the terms "therapeutically effective amounts" and "pharmaceutically effective amounts" include prophylactic or preventative amounts of the compositions of the described invention. In prophylactic or preventative applications of the described invention, pharmaceutical compositions or medicaments are administered to a patient susceptible to, or otherwise at risk of, a disease, disorder or condition resulting from accumulation of an amyloid peptide in an amount sufficient to eliminate or reduce the risk, lessen the severity, or delay the onset of the disease, disorder or condition, including biochemical, histologic and/or behavioral symptoms of the disease, disorder or condition, its complications, and intermediate pathological phenotypes presenting during development of the disease, disorder or condition.

The term "phosphorylated tau accumulation modulating amount" as used herein refers to a therapeutically effective amount of a leptin composition that modulates the phosphorylation of tau protein. A phosphorylated tau accumulation-modulating amount includes prophylactic or preventative amounts of the compositions of the described invention.

The term "cognitive function enhancing amount" as used herein refers to a therapeutically effective amount of a leptin composition (i.e., dose and frequency of administration) that modulates mental processes of perception, memory, judgment or reasoning and thereby adds to, improves, or increases mental performance in a subject as compared to a subject that has not been administered a cognitive-function enhancing amount of a composition or material.

A cognitive function enhancing amount is from about 0.01 mg/kg body weight to about 100 g/kg body weight.

According to another embodiment, the phosphorylated tau accumulation modulating amount is from about 0.01 mg/kg body weight to about 100 g/kg body weight. According to another embodiment, the phosphorylated tau accumulation modulating amount is from about 0.01 mg/kg body weight to about 95 g/kg body weight. According to another embodiment, the phosphorylated tau accumulation modulating amount is from about 0.01 mg/kg body weight to about 90 g/kg body weight. According to another embodiment, the phosphorylated tau accumulation modulating amount is from about 0.01 mg/kg body weight to about 85 g/kg body weight. According to another embodiment, the phosphorylated tau accumulation modulating amount is from about 0.01 mg/kg body weight to about 80 g/kg body weight. According to another embodiment, the phosphorylated tau accumulation modulating amount is from about 0.01 mg/kg body weight to about 75 g/kg body weight. According to another embodiment, the phosphorylated tau accumulation modulating amount is from about 0.01 mg/kg body weight to about 70 g/kg body weight. According to another embodiment, the phosphorylated tau accumulation modulating amount is from about 0.01 mg/kg body weight to about 65 g/kg body weight. According to another embodiment, the phosphorylated tau accumulation modulating amount is from about 0.01 mg/kg body weight to about 60 g/kg body weight. According to another embodiment, the phosphorylated tau accumulation modulating amount is from about 0.01 mg/kg body weight to about 55 g/kg body weight. According to another embodiment, the phosphorylated tau accumulation modulating amount is from about 0.01 mg/kg body weight to about 50 g/kg body weight. According to another embodiment, the phosphorylated tau accumulation modulating amount is from about 0.01 mg/kg body weight to about 45 g/kg body weight. According to another embodiment, the phosphorylated tau accumulation modulating amount is from about 0.01 mg/kg body weight to about 40 g/kg body weight. According to another embodiment, the phosphorylated tau accumulation modulating amount is from about 0.01 mg/kg body weight to about 35 g/kg body weight. According to another embodiment, the phosphorylated tau accumulation modulating amount is from about 0.01 mg/kg body weight to about 30 g/kg body weight. According to another embodiment, the phosphorylated tau accumulation modulating amount is from about 0.01 mg/kg body weight to about 25 g/kg body weight. According to another embodiment, the phosphorylated tau accumulation modulating amount is from about 0.01 mg/kg body weight to about 20 g/kg body weight. According to another embodiment, the phosphorylated tau accumulation modulating amount is from about 0.01 mg/kg body weight to about 15 g/kg body weight. According to another embodiment, the phosphorylated tau accumulation modulating amount is from about 0.01 mg/kg body weight to about 10 g/kg body weight. According to another embodiment, the phosphorylated tau accumulation modulating amount is from about 0.01 mg/kg body weight to about 5 g/kg body weight. According to another embodiment, the phosphorylated tau accumulation modulating amount is from about 0.01 mg/kg body weight to about 4 g/kg body weight. According to another embodiment, the phosphorylated tau accumulation modulating amount is from about 0.01 mg/kg body weight to about 3 g/kg body weight. According to another embodiment, the phosphorylated tau accumulation modulating amount is from about 0.01 mg/kg body weight to about 2 g/kg body weight. According to another embodiment, the phosphorylated tau accumulation modulating amount is from about 0.01 mg/kg body weight to about 1 g/kg body weight. According to another embodiment, the phosphorylated tau accumulation modulating amount is from about 0.01 mg/kg body weight to about 500 mg/kg body weight. According to another embodiment, the phosphorylated tau accumulation modulating amount is from about 0.01 mg/kg body weight to about 250 mg/kg body weight. According to another embodiment, the phosphorylated tau accumulation modulating amount is from about 0.01 mg/kg body weight to about 100 mg/kg body weight. According to another embodiment, the phosphorylated tau accumulation modulating amount is from about 0.01 mg/kg body weight to about 50 mg/kg body weight. According to another embodiment, the phosphorylated tau accumulation modulating amount is from about 0.01 mg/kg body weight to about 25 mg/kg body weight. According to another embodiment, the phosphorylated tau accumulation modulating amount is from about 0.01 mg/kg body weight to about 10 mg/kg body weight. According to another embodiment, the phosphorylated tau accumulation modulating amount is from about 0.01 mg/kg body weight to about 5 mg/kg body weight. According to another embodiment, the phosphorylated tau accumulation modulating amount is from about 0.01 mg/kg body weight to about 1 mg/kg body weight.

The term "therapeutic agent" as used herein refers to a drug, molecule, nucleic acid, protein, composition or other substance that provides a therapeutic effect. The term "active" as used herein refers to the ingredient, component or constituent of the compositions of the present invention responsible for the intended therapeutic effect. The terms "therapeutic agent" and "active agent" are used interchangeably herein. The active agent may be a therapeutically effective amount of at least one of a leptin, a leptin mimic, a leptin derivative, or a leptin agonist or a pharmaceutically acceptable salt thereof The term "therapeutic component" as used herein refers to a therapeutically effective dosage (i.e., dose and frequency of administration) that eliminates, reduces, or prevents the progression of a particular disease manifestation in a percentage of a population. An example of a commonly used therapeutic component is the ED50, which describes the dose in a particular dosage that is therapeutically effective for a particular disease manifestation in 50% of a population.

The term "therapeutic effect" as used herein refers to a consequence of treatment, the results of which are judged to be desirable and beneficial. A therapeutic effect may include, directly or indirectly, the arrest, reduction, or elimination of a disease manifestation. A therapeutic effect also may include, directly or indirectly, the arrest reduction or elimination of the progression of a disease manifestation.

The term "drug" as used herein refers to a therapeutic agent or any substance, other than food, used in the prevention, diagnosis, alleviation, treatment, or cure of disease.

The compositions described herein are isolated molecules. An "isolated molecule" is a molecule that is substantially pure and is free of other substances with which it is ordinarily found in nature or in vivo systems to an extent practical and appropriate for its intended use. In particular, the compositions are sufficiently pure and are sufficiently free from other biological constituents of host cells so as to be useful in, for example, producing pharmaceutical preparations or sequencing if the composition is a nucleic acid, peptide, or polysaccharide. Because compositions may be admixed with a pharmaceutically-acceptable carrier in a pharmaceutical preparation, the compositions may comprise only a small percentage by weight of the preparation. The composition is nonetheless substantially pure in that it has been substantially separated from the substances with which it may be associated in living systems or during synthesis. As used herein, the term "substantially pure" refers purity of at least 75%, at least 80%, at least 85%, at least 90%, at least 95% or at least 99% pure as determined by an analytical protocol. Such protocols may include, for example, but are not limited to, FACS, HPLC, gel electrophoresis, chromatography, and the like.

The leptin composition and/or the first composition may be combined with other therapeutic agents and administered locally. The leptin composition and/or first composition and other therapeutic agent(s) may be administered simultaneously or sequentially. When the other therapeutic agents are administered simultaneously, they can be administered in the same or separate formulations, but are administered at the same time. The other therapeutic agents are administered sequentially with one another and with leptin composition and/or first composition when the administration of the other therapeutic agents and the inhibitor is temporally separated. The separation in time between the administration of these agents may be a matter of minutes or it may be longer. The therapeutic agents may be a leptin antagonist, a leptin blocker, a leptin blocker, or an leptin antagonist, or combinations thereof.

According to another embodiment, the leptin composition and/or the first composition further comprises a second therapeutic agent. According to some such embodiments, the second therapeutic agent is an antibiotic agent. According to some such embodiments, the second therapeutic agent is an anti-fungal agent. According to some such embodiments, the second therapeutic agent is an anti-viral agent. According to some such embodiments, the second therapeutic agent is an anti-protozoal agent. According to some such embodiments, the second therapeutic agent is a steroidal anti-inflammatory agent. According to some such embodiments, the second therapeutic agent is a non-steroidal anti-inflammatory agent. According to some such embodiments, the second therapeutic agent is an anti-oxidant agent. According to some such embodiments, the second therapeutic agent is a hormone. According to some such embodiments, the second therapeutic agent is a vitamin. According to some such embodiments, the second therapeutic agent is an antihistamine agent. According to some such embodiments, the second therapeutic agent is a chemotherapeutic agent.

The term "antibiotic agent" as used herein means any of a group of chemical substances having the capacity to inhibit the growth of, or to destroy bacteria, and other microorganisms, used chiefly in the treatment of infectious diseases. Examples of antibiotic agents include, but are not limited to, Penicillin G; Methicillin; Nafcillin; Oxacillin; Cloxacillin; Dicloxacillin; Ampicillin; Amoxicillin; Ticarcillin; Carbenicillin; Mezlocillin; Azlocillin; Piperacillin; Imipenem; Aztreonam; Cephalothin; Cefaclor; Cefoxitin; Cefuroxime; Cefonicid; Cefinetazole; Cefotetan; Cefprozil; Loracarbef; Cefetamet; Cefoperazone; Cefotaxime; Ceftizoxime; Ceftriaxone; Ceftazidime; Cefepime; Cefixime; Cefpodoxime; Cefsulodin; Fleroxacin; Nalidixic acid; Norfloxacin; Ciprofloxacin; Ofloxacin; Enoxacin; Lomefloxacin; Cinoxacin; Doxycycline; Minocycline; Tetracycline; Amikacin; Gentamicin; Kanamycin; Netilmicin; Tobramycin; Streptomycin; Azithromycin; Clarithromycin; Erythromycin; Erythromycin estolate; Erythromycin ethyl succinate; Erythromycin glucoheptonate; Erythromycin lactobionate; Erythromycin stearate; Vancomycin; Teicoplanin; Chloramphenicol; Clindamycin; Trimethoprim; Sulfamethoxazole; Nitrofurantoin; Rifampin; Mupirocin; Metronidazole; Cephalexin; Roxithromycin; Co-amoxiclavuanate; combinations of Piperacillin and Tazobactam; and their various salts, acids, bases, and other derivatives. Anti-bacterial antibiotic agents include, but are not limited to, penicillins, cephalosporins, carbacephems, cephamycins, carbapenems, monobactams, aminoglycosides, glycopeptides, quinolones, tetracyclines, macrolides, and fluoroquinolones.

The term "anti-fungal agent" as used herein means any of a group of chemical substances having the capacity to inhibit the growth of or to destroy fungi. Anti-fungal agents include but are not limited to Amphotericin B, Candicidin, Dermostatin, Filipin, Fungichromin, Hachimycin, Hamycin, Lucensomycin, Mepartricin, Natamycin, Nystatin, Pecilocin, Perimycin, Azaserine, Griseofulvin, Oligomycins, Neomycin, Pyrrolnitrin, Siccanin, Tubercidin, Viridin, Butenafine, Naftifine, Terbinafine, Bifonazole, Butoconazole, Chlordantoin, Chlormidazole, Cloconazole, Clotrimazole, Econazole, Enilconazole, Fenticonazole, Flutrimazole, Isoconazole, Ketoconazole, Lanoconazole, Miconazole, Omoconazole, Oxiconazole, Sertaconazole, Sulconazole, Tioconazole, Tolciclate, Tolindate, Tolnaftate, Fluconawle, Itraconazole, Saperconazole, Terconazole, Acrisorcin, Amorolfine, Biphenamine, Bromosalicylchloranilide, Buclosamide, Calcium Propionate, Chlorphenesin, Ciclopirox, Cloxyquin, Coparaffinate, Diamthazole, Exalamide, Flucytosine, Halethazole, Hexetidine, Loflucarban, Nifuratel, Potassium Iodide, Propionic Acid, Pyrithione, Salicylanilide, Sodium Propionate, Sulbentine, Tenonitrozole, Triacetin, Ujothion, Undecylenic Acid, and Zinc Propionate.

The term "anti-viral agent" as used herein means any of a group of chemical substances having the capacity to inhibit the replication of or to destroy viruses used chiefly in the treatment of viral diseases. Anti-viral agents include, but are not limited to, Acyclovir, Cidofovir, Cytarabine, Dideoxyadenosine, Didanosine, Edoxudine, Famciclovir, Floxuridine, Ganciclovir, Idoxuridine, Inosine Pranobex, Lamivudine, MADU, Penciclovir, Sorivudine, Stavudine, Trifluridine, Valacyclovir, Vidarabine, Zalcitabine, Zidovudine, Acemannan, Acetylleucine, Amantadine, Amidinomycin, Delavirdine, Foscarnet, Indinavir, Interferons (e.g., IFN-alpha), Kethoxal, Lysozyme, Methisazone, Moroxydine, Nevirapine, Podophyllotoxin, Ribavirin, Rimantadine, Ritonavir2, Saquinavir, Stailimycin, Statolon, Tromantadine, Zidovudine (AZT) and Xenazoic Acid.

The term "anti-protozoal agent" as used herein means any of a group of chemical substances having the capacity to inhibit the growth of or to destroy protozoans used chiefly in the treatment of protozoal diseases. Examples of antiprotozoal agents, without limitation include pyrimethamine (Daraprim®) sulfadiazine, and Leucovorin.

"Steroidal anti-inflammatory agent", as used herein, refer to any one of numerous compounds containing a 17-carbon 4-ring system and includes the sterols, various hormones (as anabolic steroids), and glycosides. Representative examples of steroidal anti-inflammatory drugs include, without limitation, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chloroprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

"Non-steroidal anti-inflammatory agents" refers to a large group of agents that are aspirin-like in their action, including ibuprofen (Advil)®, naproxen sodium (Aleve)®, and acetaminophen (Tylenol)®. Additional examples of non-steroidal anti-inflammatory agents that are usable in the context of the present invention include, without limitation, oxicams, such as piroxicam, isoxicam, tenoxicam, sudoxicam, and CP-14,304; disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed, as well as the dermatologically acceptable salts and esters of these agents. For example, etofenamate, a flufenamic acid derivative, is particularly useful for topical application.

"An anti-oxidant agent" as used herein refers to a substance that inhibits oxidation or reactions promoted by oxygen or peroxides. Non-limiting examples of anti-oxidants that are usable in the context of the present invention include ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the tradename Trolox®), gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, glycine pidolate, arginine pilolate, nordihydroguaiaretic acid, bioflavonoids, curcumin, lysine, methionine, proline, super-oxide dismutase, silymarin, tea extracts, grape skin/seed extracts, melanin, and rosemary extracts.

"Chemotherapeutic agent" refers to chemicals useful in the treatment or control of a disease. Non-limiting examples of chemotherapeutic agents usable in context of the present invention include daunorubicin, doxorubicin, idarubicin, amrubicin, pirarubicin, epirubicin, mitoxantrone, etoposide, teniposide, vinblastine, vincristine, mitomycin C, 5-FU, paclitaxel, docetaxel, actinomycin D, colchicine, topotecan, irinotecan, gemcitabine cyclosporin, verapamil, valspodor, probenecid, MK571, GF120918, LY335979, biricodar, terfenadine, quinidine, pervilleine A and XR9576.

"Antihistamine agent" as used herein refers to any of various compounds that counteract histamine in the body and that are used for treating allergic reactions (such as hay fever) and cold symptoms. Non-limiting examples of antihistamines usable in context of the present invention include chlorpheniramine, brompheniramine, dexchlorpheniramine, tripolidine, clemastine, diphenhydramine, promethazine, piperazines, piperidines, astemizole, loratadine and terfenadine.

"Vitamin" as used herein, refers to any of various organic substances essential in minute quantities to the nutrition of most animals act especially as coenzymes and precursors of coenzymes in the regulation of metabolic processes. Non-limiting examples of vitamins usable in context of the present invention include vitamin A and its analogs and derivatives: retinol, retinal, retinyl palmitate, retinoic acid, tretinoin, isotretinoin (known collectively as retinoids), vitamin E (tocopherol and its derivatives), vitamin C (L-ascorbic acid and its esters and other derivatives), vitamin $B_3$ (niacinamide and its derivatives), alpha hydroxy acids (such as glycolic acid, lactic acid, tartaric acid, malic acid, citric acid, etc.) and beta hydroxy acids (such as salicylic acid and the like).

"Hormone" as used herein refers to natural substances produced by organs of the body that travel by blood to trigger activity in other locations or their synthetic analogs. Suitable hormones for use in the context of the present invention include, but are not limited to, any hormone produced by neurosecretory cells, including gonadotropin releasing hormone (GnRH), corticotropin releasing hormone (CRH), thyrotropin releasing hormone (TRH), prolactin inhibiting hormone (dopamine) and orexin (hypocretin), as well as recombinant hormones, meaning hormones produced by a process using DNA engineered to contain sequences that normally would not occur together and introducing that DNA into the cells of a host.

Neurofibrillary tangles ("NFT") generally refer to aggregates of the microtubule-associated protein "tau", which have become hyperphosphorylated and accumulate inside the cells themselves.

According to one embodiment, the progressive cognitive disorder comprises accumulation of neurofibrillary tangles in brain. According to another embodiment, the progressive cognitive disorder is Alzheimer's Disease. According to another embodiment, progressive cognitive disorder is progressive supranuclear palsy. According to another embodiment, progressive cognitive disorder is dementia. According to another embodiment, progressive cognitive disorder is dementia pugilistica. According to another embodiment, progressive cognitive disorder is Creutzfeldt-Jakob disease. According to another embodiment, progressive cognitive disorder is frontotemporal dementia. According to another embodiment, progressive cognitive disorder is Pick's disease. According to another embodiment, progressive cognitive disorder is FTDP-17 (parkinsonism) corticobasal degeneration. According to another aspect, the present invention provides a method of improving resilience of cognitive function in a subject in need thereof, the method comprising the step of (a) administering to the subject a composition comprising: (i) a cognitive function-enhancing amount of a leptin composition; and (ii) a pharmaceutically acceptable carrier; and (b) modulating accumulation of phosphorylated tau in cerebrospinal fluid of the subject.

The term "resilience" as used herein refers to the ability to return to the original form, position, or function after or during an illness, condition, disease, syndrome or disorder.

According to one embodiment of the method, the leptin composition comprises a leptin, or a pharmaceutically acceptable salt thereof. According to another embodiment, the leptin composition comprises a leptin mimic, or a pharmaceutically acceptable salt thereof. According to another embodiment, the leptin composition comprises a leptin derivative, or a pharmaceutically acceptable salt thereof. According to another embodiment, the leptin composition comprises an AMP-dependent protein kinase activator, or a pharmaceutically acceptable salt thereof. According to another embodiment, the leptin composition comprises a leptin agonist, or a pharmaceutically acceptable salt thereof. According to another embodiment, the leptin composition comprises a leptin blocker, or a pharmaceutically acceptable salt thereof. According to another embodiment, the leptin composition comprises a mimic of a leptin blocker, or a pharmaceutically acceptable salt thereof. According to another embodiment, the leptin composition comprises a leptin antagonist, or a pharmaceutically acceptable salt thereof. According to another embodiment, the leptin composition comprises an AMP-dependent protein kinase inhibitor.

According to another embodiment, the leptin composition further comprises a second therapeutic agent. According to some such embodiments, the second therapeutic agent is an antibiotic. According to some such embodiments, the second therapeutic agent is an anti-fungal agent. According to some such embodiments, the second therapeutic agent is an anti-viral agent. According to some such embodiments, the second therapeutic agent is an anti-protozoal agent. According to some such embodiments, the second therapeutic agent is a non-steroidal anti-inflammatory agent. According to some such embodiments, the second therapeutic agent is an antioxidant. According to some such embodiments, the second therapeutic agent is a steroidal anti-inflammatory agent. According to some such embodiments, the second therapeutic agent is a hormone. According to some such embodiments, the second therapeutic agent is a vitamin. According to some such embodiments, the second therapeutic agent is an anti-histamine agent. According to some such embodiments, the second therapeutic agent is an chemotherapeutic agent.

Compositions

The compositions are delivered in therapeutically effective amounts. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen may be planned which does not cause substantial toxicity and yet is effective to treat the particular subject. The effective amount for any particular application may vary depending on such factors as the disease or condition being treated, the particular therapeutically active leptin, leptin mimic, leptin agonist, leptin derivative peptide, leptin blocker and/or leptin antagonist, or combinations thereof, being administered, the size of the subject, or the severity of the disease or condition. One of ordinary skill in the art may determine empirically the effective amount of a particular leptin composition and/or other therapeutic agent without necessitating undue experimentation. It generally is preferred that a maximum dose be used, that is, the highest safe dose according to some medical judgment. "Dose" and "dosage" are used interchangeably herein.

For any compound described herein the therapeutically effective amount initially may be determined from preliminary in vitro studies and/or animal models. A therapeutically effective dose may also be determined from human data for a therapeutically active leptin, a leptin mimic, a leptin agonist, a leptin derivative peptide, a leptin blocker and/or a leptin antagonist, or combinations thereof, which have been tested in humans and for compounds which are known to exhibit similar pharmacological activities, such as other related active agents. The applied dose may be adjusted based on the relative bioavailability and potency of the administered compound or composition. Adjusting the dose to achieve maximal efficacy based on the methods described above and other methods as are well-known in the art is well within the capabilities of the ordinarily skilled artisan.

The formulations of a first composition, a leptin composition, a therapeutically active leptin, a leptin mimic, a leptin agonist, a leptin derivative peptide, a leptin blocker and/or a leptin antagonist, or combinations thereof, may be administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the first composition, and/or a leptin composition, a therapeutically active leptin, a leptin mimic, a leptin agonist, a leptin derivative peptide, a leptin blocker and/or a leptin antagonist, or combinations thereof, may be administered to a subject by any mode that delivers the leptin composition and/or the first composition to the desired surface. Administering the pharmaceutical composition may be accomplished by any means known to the skilled artisan. Routes of administration include, but are not limited to, intrathecal, intra-arterial, parenteral (e.g. intravenous), or intramuscular, orally, buccally, intranasally, rectally, or topically.

The inhibitors and other therapeutics may be delivered to a subject during surgery to treat an underlying condition or side effect such as subarachnoid hemorrhage or peripheral vasospasm or during intra-arterial procedures.

Oral Compositions

The compositions of the present invention may be in a form suitable for oral use, for example, as tablets, troches, lozenges, aqueous or oily suspensions, dispersible powders or granules, emulsions, hard or soft capsules or syrups or elixirs. As used herein, the terms "oral" or "orally" refer to the introduction into the body by mouth whereby absorption occurs in one or more of the following areas of the body: the mouth, stomach, small intestine, lungs (also specifically referred to as inhalation), and the small blood vessels under the tongue (also specifically referred to as sublingually). Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient(s) in admixture with non-toxic pharmaceutically-acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch or alginic acid; binding agents, for example, starch, gelatin or acacia; and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They also may be coated for controlled release.

Compositions of the present invention also may be formulated for oral use as hard gelatin capsules, where the active ingredient(s) is(are) mixed with an inert solid diluent, for example, calcium carbonate, calcium phosphate or kaolin, or soft gelatin capsules wherein the active ingredient(s) is (are) mixed with water or an oil medium, for example, peanut oil, liquid paraffin, or olive oil.

The compositions of the present invention may be formulated as aqueous suspensions wherein the active ingredient(s) is (are) in admixture with excipients suitable for the manufacture of aqueous suspensions. Such excipients are suspending agents, for example, sodium carboxymethylcellulose, methylcellulose, hydroxy-propylmethylcellulose, sodium alginate, polyvinylpyrrolidone, gum tragacanth, and gum acacia; dispersing or wetting agents may be a naturally-occurring phosphatide such as lecithin, or condensation products of an alkylene oxide with fatty acids, for example, polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions also may contain one or more coloring agents, one or more flavoring agents, and one or more sweetening agents, such as sucrose or saccharin.

Compositions of the present invention may be formulated as oily suspensions by suspending the active ingredient in a vegetable oil, for example arachis oil, olive oil, sesame oil or coconut oil, or in a mineral oil, such as liquid paraffin. The oily suspensions may contain a thickening agent, for example, beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Compositions of the present invention may be formulated in the form of dispersible powders and granules suitable for preparation of an aqueous suspension by the addition of water. The active ingredient in such powders and granules is provided in admixture with a dispersing or wetting agent, suspending agent, and one or more preservatives. Suitable dispersing or wetting agents and suspending agents are exemplified by those already mentioned above. Additional excipients, for example, sweetening, flavoring and coloring agents, also may be present.

The compositions of the invention also may be in the form of an emulsion. An emulsion is a two-phase system prepared by combining two immiscible liquid carriers, one of which is disbursed uniformly throughout the other and consists of globules that have diameters equal to or greater than those of the largest colloidal particles. The globule size is critical and must be such that the system achieves maximum stability. Usually, separation of the two phases will not occur unless a third substance, an emulsifying agent, is incorporated. Thus, a basic emulsion contains at least three components, the two immiscible liquid carriers and the emulsifying agent, as well as the active ingredient. Most emulsions incorporate an aqueous phase into a non-aqueous phase (or vice versa). However, it is possible to prepare emulsions that are basically non-aqueous, for example, anionic and cationic surfactants of the non-aqueous immiscible system glycerin and olive oil. Thus, the compositions of the invention may be in the form of an oil-in-water emulsion. The oily phase may be a vegetable oil, for example, olive oil or arachis oil, or a mineral oil, for example a liquid paraffin, or a mixture thereof. Suitable emulsifying agents may be naturally-occurring gums, for example, gum acacia or gum tragacanth, naturally-occurring phosphatides, for example soy bean, lecithin, and esters or partial esters derived from fatty acids and hexitol anhydrides, for example sorbitan monooleate, and condensation products of the partial esters with ethylene oxide, for example, polyoxyethylene sorbitan monooleate. The emulsions also may contain sweetening and flavoring agents.

The compositions of the invention also may be formulated as syrups and elixirs. Syrups and elixirs may be formulated with sweetening agents, for example, glycerol, propylene glycol, sorbitol or sucrose. Such formulations also may contain a demulcent, a preservative, and flavoring and coloring agents. Demulcents are protective agents employed primarily to alleviate irritation, particularly mucous membranes or abraded (meaning torn or cut) tissues. A number of chemical substances possess demulcent properties. These substances include the alginates, mucilages, gums, dextrins, starches, certain sugars, and polymeric polyhydric glycols. Others include acacia, agar, benzoin, carbomer, gelatin, glycerin, hydroxyethyl cellulose, hydroxypropyl cellulose, hydroxypropyl methylcellulose, propylene glycol, sodium alginate, tragacanth, hydrogels and the like.

Buccal Compositions

For buccal administration, the compositions of the present invention may take the form of tablets or lozenges formulated in a conventional manner.

Parenteral Compositions

The compositions of the present invention may be in the form of a sterile injectable aqueous or oleaginous suspension. The term "parenteral" as used herein refers to introduction into the body by way of an injection (i.e., administration by injection), including, for example, subcutaneously (i.e., an injection beneath the skin), intramuscularly (i.e., an injection into a muscle), intravenously (i.e., an injection into a vein), intrathecally (i.e., an injection into the space around the spinal cord), intrasternal injection, or infusion techniques. A parenterally administered composition of the present invention is delivered using a needle, e.g., a surgical needle. The term "surgical needle" as used herein, refers to any needle adapted for delivery of fluid (i.e., capable of flow) compositions of the present invention into a selected anatomical structure. Injectable preparations, such as sterile injectable aqueous or oleaginous suspensions, may be formulated according to the known art using suitable dispersing or wetting agents and suspending agents.

The first composition and/or leptin composition, therapeutically active leptin, leptin mimic, leptin agonist, leptin derivative peptide, leptin blocker and/or leptin antagonist, when it is desirable to deliver them locally, may be formulated for parenteral administration by injection, e.g., by bolus injection or continuous infusion. Formulations for injection may be presented in unit dosage form, for example, in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension also may contain suitable stabilizers or agents which increase the solubility of the compounds to allow for the preparation of highly concentrated solutions. Alternatively, the active compounds may be in powder form for constitution with a suitable vehicle, e.g., sterile pyrogen-free water, before use.

The pharmaceutical compositions also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Suitable liquid or solid pharmaceutical preparation forms are, for example, microencapsulated, and if appropriate, with one or more excipients, encochleated, coated onto microscopic gold particles, contained in liposomes, pellets for implantation into the tissue, or dried onto an object to be rubbed into the tissue. Such pharmaceutical compositions also may be in the form of granules, beads, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, or solubilizers are customarily used as described above. The pharmaceutical compositions are suitable for use in a variety of drug delivery systems. For a brief review of methods for drug delivery, see Langer 1990 Science 249, 1527-1533, which is incorporated herein by reference.

The first composition and/or leptin composition, therapeutically active leptin, leptin mimic, leptin agonist, leptin derivative peptide, leptin blocker and/or leptin antagonist, or combinations thereof, and optionally other therapeutics may be administered per se (neat) or in the form of a pharmaceutically acceptable salt. Other therapeutics may include, but are not limited to, an antibiotic agent, an anti-fungal agent, an anti-viral agent, an anti-protozoal agent, a steroidal anti-inflammatory agent, a non-steroidal anti-inflammatory agent, an anti-oxidant agent, a hormone, a vitamin, an antihistamine agent, a chemotherapeutic agent, or combinations thereof. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts may be prepared as alkaline metal or alkaline earth salts, such as sodium, potassium or calcium salts of the carboxylic acid group. By "pharmaceutically acceptable salt" is meant those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, P. H. Stahl, et al. describe pharmaceutically acceptable salts in detail in "Handbook of Pharmaceutical Salts: Properties, Selection, and Use" (Wiley VCH, Zurich, Switzerland: 2002). The salts may be prepared in situ during the final isolation and purification of the compounds described within the present invention or separately by reacting a free base function with a suitable organic acid. Representative acid addition salts include, but are not limited to, acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, fumarate, hydrochloride, hydrobromide, hydroiodide, 2-hydroxyethansulfonate(isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups may be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid. Basic addition salts may be prepared in situ during the final isolation and purification of compounds described within the invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like. Pharmaceutically acceptable salts also may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium or magnesium) salts of carboxylic acids also may be made.

The formulations may be presented conveniently in unit dosage form and may be prepared by any of the methods well known in the art of pharmacy. All methods include the step of bringing into association a leptin composition, a therapeutically active leptin, a leptin mimic, a leptin agonist, a leptin derivative peptide, a leptin blocker and/or a leptin antagonist, or combinations thereof, or a pharmaceutically acceptable salt or solvate thereof ("active compound") with the carrier which constitutes one or more accessory agents. In general, the formulations are prepared by uniformly and intimately bringing into association the active agent with liquid carriers or finely divided solid carriers or both and then, if necessary, shaping the product into the desired formulation.

The pharmaceutical agent or a pharmaceutically acceptable ester, salt, solvate or prodrug thereof may be mixed with other active materials that do not impair the desired action, or with materials that supplement the desired action. Solutions or suspensions used for parenteral, intradermal, subcutaneous, intrathecal, or topical application may include, but are not limited to, for example, the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation may be enclosed in ampoules, disposable syringes or multiple dose vials made of glass or plastic. Administered intravenously, particular carriers are physiological saline or phosphate buffered saline (PBS).

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

These compositions may also contain adjuvants including preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

Suspensions, in addition to the active compounds, may contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

Injectable depot forms are made by forming microencapsulated matrices of the drug in biodegradable polymers such as polylactide-polyglycolide. Depending upon the ratio of drug to polymer and the nature of the particular polymer employed, the rate of drug release may be controlled. Such long acting formulations may be formulated with suitable polymeric or hydrophobic materials (for example as an emulsion in an acceptable oil) or ion exchange resins, or as sparingly soluble derivatives, for example, as a sparingly soluble salt. Examples of other biodegradable polymers include poly (orthoesters) and poly(anhydrides). Depot injectable formulations are also prepared by entrapping the drug in liposomes or microemulsions which are compatible with body tissues.

The locally injectable formulations may be sterilized, for example, by filtration through a bacterial-retaining filter or by incorporating sterilizing agents in the form of sterile solid compositions that may be dissolved or dispersed in sterile water or other sterile injectable medium just prior to use. Injectable preparations, for example, sterile injectable aqueous or oleaginous suspensions may be formulated according to the known art using suitable dispersing or wetting agents and suspending agents. The sterile injectable preparation also may be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils conventionally are employed or as a solvent or suspending medium. For this purpose any bland fixed oil may be employed including synthetic mono- or diglycerides. In addition, fatty acids such as oleic acid are used in the preparation of injectables.

Formulations for parenteral (including but not limited to, subcutaneous, intradermal, intramuscular, intravenous, intrathecal and intraarticular) administration include aqueous and non-aqueous sterile injection solutions that may contain anti-oxidants, buffers, bacteriostats and solutes, which render the formulation isotonic with the blood of the intended recipient; and aqueous and non-aqueous sterile suspensions, which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example, saline, water-for-injection, immediately prior to use. Extemporaneous injection solutions and suspensions may be prepared from sterile powders, granules and tablets of the kind previously described.

Another method of formulation of the compositions described herein involves conjugating the compounds described herein to a polymer that enhances aqueous solubility. Examples of suitable polymers include but are not limited to polyethylene glycol, poly-(d-glutamic acid), poly-(1-glutamic acid), poly-(1-glutamic acid), poly-(d-aspartic acid), poly-(1-aspartic acid), poly-(1-aspartic acid) and copolymers thereof. Polyglutamic acids having molecular weights between about 5,000 to about 100,000, with molecular weights between about 20,000 and about 80,000 may be used and with molecular weights between about 30,000 and about 60,000 may also be used.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The therapeutic agent(s), including the leptin composition, therapeutically active leptin, leptin mimic, leptin agonist, leptin derivative peptide, leptin blocker and/or leptin antagonist, or combinations thereof, may be provided in particles. The term "particles" as used herein refers to nano- or microparticles (or in some instances larger) that may contain in whole or in part the leptin composition, therapeutically active leptin, leptin mimic, leptin agonist, leptin derivative peptide, leptin blocker and/or leptin antagonist, or combinations thereof, or the other therapeutic agent(s) as described herein, including, but not limited to, an antibiotic agent, an anti-fungal agent, an anti-viral agent, an anti-protozoal agent, a steroidal anti-inflammatory agent, a non-steroidal anti-inflammatory agent, an anti-oxidant agent, a hormone, a vitamin, an antihistamine agent, a chemotherapeutic agent, or combinations thereof. The particles may contain the therapeutic agent(s) in a core surrounded by a coating. The therapeutic agent(s) also may be dispersed throughout the particles. The therapeutic agent(s) also may be adsorbed into the particles. The particles may be of any order release kinetics, including zero order release, first order release, second order release, delayed release, sustained release, immediate release, etc., and any combination thereof. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules that contain the leptin composition, therapeutically active leptin, leptin mimic, leptin agonist, leptin derivative peptide, leptin blocker and/or leptin antagonist, or combinations thereof, in a solution or in a semi-solid state. The particles may be of virtually any shape.

Both non-biodegradable and biodegradable polymeric materials may be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels as described by Sawhney et al in Macromolecules (1993) 26, 581-587, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Insufflation Compositions

The compositions of the present invention may be in the form of a dispersible dry powder for delivery by inhalation or insufflation (either through the mouth or through the nose). Dry powder compositions may be prepared by processes known in the art, such as lyophilization and jet milling, as disclosed in International Patent Publication No. WO 91/16038 and as disclosed in U.S. Pat. No. 6,921,527, the disclosures of which are incorporated by reference. Spray drying, for example, is a process in which a homogeneous aqueous mixture of drug and the carrier is introduced via a nozzle (e.g., a two fluid nozzle), spinning disc or an equivalent device into a hot gas stream to atomize the solution to form fine droplets. The aqueous mixture may be a solution, suspension, slurry, or the like, but needs to be homogeneous to ensure uniform distribution of the components in the mixture and ultimately the powdered composition. The solvent, generally water, rapidly evaporates from the droplets producing a fine dry powder having particles from about 1 µm to 5 µm in diameter. The spray drying is done under conditions that result in a substantially amorphous powder of homogeneous constitution having a particle size that is respirable, a low moisture content and flow characteristics that allow for ready aerosolization. Preferably the particle size of the resulting powder is such that more than about 98% of the mass is in particles having a diameter of about 10 µm or less with about 90% of the mass being in particles having a diameter less than 5 µm. Alternatively, about 95% of the mass will have particles with a diameter of less than 10 µm with about 80% of the mass of the particles having a diameter of less than 5 µm. Dry powder compositions also may be prepared by lyophilization and jet milling, as disclosed in International Patent Publication No. WO 91/16038, the disclosure of which are incorporated by reference.

The term "dispersibility" or "dispersible" means a dry powder having a moisture content of less than about 10% by weight (% w) water, usually below about 5% w and preferably less than about 3% w; a particle size of about 1.0-5.0 µm mass median diameter (MMD), usually 1.0-4.0 µm MMD, and preferably 1.0-3.0 µm MMD; a delivered dose of about >30%, usually >40%, preferably >50%, and most preferred >60%; and an aerosol particle size distribution of about 1.0-5.0 µm mass median aerodynamic diameter (MMAD), usually 1.5-4.5 µm MMAD, and preferably 1.5-4.0 µm MMAD. Methods and compositions for improving dispersibility are disclosed in U.S. application Ser. No. 08/423,568, filed Apr. 14, 1995, the disclosure of which is hereby incorporated by reference.

The term "powder" means a composition that consists of finely dispersed solid particles that are free flowing and capable of being readily dispersed in an inhalation device and subsequently inhaled by a subject so that the particles reach the lungs to permit penetration into the alveoli. Thus, the powder is said to be "respirable." Preferably the average particle size is less than about 10 microns (µm) in diameter with a relatively uniform spheroidal shape distribution. More preferably the diameter is less than about 7.5 µm and most preferably less than about 5.0 µm. Usually the particle size distribution is between about 0.1 µm and about 5 µm in diameter, particularly about 0.3 µm to about 5 µm.

The term "dry" means that the composition has a moisture content such that the particles are readily dispersible in an inhalation device to form an aerosol. This moisture content is generally below about 10% by weight (% w) water, usually below about 5% w and preferably less than about 3% w.

The amount of the pharmaceutically acceptable carrier is that amount needed to provide the necessary stability, dispersibility, consistency and bulking characteristics to ensure a uniform pulmonary delivery of the composition to a subject in need thereof. Numerically the amount may be from about 0.05% w to about 99.95% w, depending on the activity of the drug being employed. Preferably about 5% w to about 95% will be used. The carrier may be one or a combination of two or more pharmaceutical excipients, but generally will be substantially free of any "penetration enhancers." Penetration enhancers are surface active compounds which promote penetration of a drug through a mucosal membrane or lining and are proposed for use in intranasal, intrarectal, and intravaginal drug formulations. Exemplary penetration enhancers include bile salts, e.g., taurocholate, glycocholate, and deoxycholate; fusidates, e.g., taurodehydrofusidate; and biocompatible detergents, e.g., Tweens, Laureth-9, and the like. The use of penetration enhancers in formulations for the lungs, however, is generally undesirable because the epithelial blood barrier in the lung can be adversely affected by such surface active compounds. The dry powder compositions of the present invention are readily absorbed in the lungs without the need to employ penetration enhancers.

The types of pharmaceutical excipients that are useful as carriers for pulmonary delivery include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Bulking agents that are particularly valuable for pulmonary delivery include compatible carbohydrates, polypeptides, amino acids or combinations thereof. Suitable carbohydrates include monosaccharides such as galactose, D-mannose, sorbose, and the like; disaccharides, such as lactose, trehalose, and the like; cyclodextrins, such as 2-hydroxypropyl-β-cyclodextrin; and polysaccharides, such as raffinose, maltodextrins, dextrans, and the like; alditols, such as mannitol, xylitol, and the like. A preferred group of carbohydrates includes lactose, trehalose, raffinose, maltodextrins, and mannitol. Suitable polypeptides include aspartame. Amino acids include alanine and glycine, with glycine being preferred.

Additives, which are minor components of the composition for pulmonary delivery, may be included for conformational stability during spray drying and for improving dispersibility of the powder. These additives include hydrophobic amino acids such as tryptophan, tyrosine, leucine, phenylalanine, and the like.

For delivery by inhalation or insufflation, the composition of the present invention is placed within a suitable dosage receptacle in an amount sufficient to provide a subject with a unit dosage treatment. The dosage receptacle is one that fits within a suitable inhalation device to allow for the aerosolization of the dry powder composition by dispersion into a gas stream to form an aerosol and then capturing the aerosol so produced in a chamber having a mouthpiece attached for subsequent inhalation by a subject in need of treatment. Such a dosage receptacle includes any container enclosing the composition known in the art such as gelatin or plastic capsules with a removable portion that allows a stream of gas (for example, air) to be directed into the container to disperse the dry powder composition. Such containers are exemplified by those shown in U.S. Pat. No. 4,227,522; U.S. Pat. No. 4,192,309; and U.S. Pat. No. 4,105,027. Suitable containers also include those used in conjunction with Glaxo's Ventolin® Rotohaler brand powder inhaler or Fison's Spinhaler® brand powder inhaler. Another suitable unit-dose container which provides a superior moisture barrier is formed from an aluminum foil plastic laminate. The pharmaceutical-based powder is filled by weight or by volume into the depression in the formable foil and hermetically sealed with a covering foil-plastic laminate. Such a container for use with a powder inhalation device is described in U.S. Pat. No. 4,778,054 and is used with Glaxo's Diskhaler (U.S. Pat. Nos. 4,627,432; 4,811,731; and 5,035,237). All of these references are incorporated herein by reference.

The compositions of the invention may be used in the form of drops or sprays (e.g., a nasal spray, aerosol spray, or pump spray) or other vehicles for nasal administration (intranasal delivery). Aerosol spray preparations can be contained in a pressurized container with a suitable propellant such as a hydrocarbon propellant. Pump spray dispensers can dispense a metered dose or a dose having a specific particle or droplet size. Any dispensing device can be arranged to dispense only a single dose, or a multiplicity of doses. More generally, compositions of the invention, especially those formulated for intranasal administration, can also be provided as solutions, suspensions, or viscous compositions (e.g., gels, lotions, creams, or ointments).

Rectal Compositions

The compositions of the present invention may be in the form of suppositories for rectal administration of the composition. "Rectal" or "rectally" as used herein refers to introduction into the body through the rectum where absorption occurs through the walls of the rectum. These compositions can be prepared by mixing the drug with a suitable nonirritating excipient such as cocoa butter and polyethylene glycols which are solid at ordinary temperatures but liquid at the rectal temperature and will therefore melt in the rectum and release the drug. When formulated as a suppository the compositions of the invention may be formulated with traditional binders and carriers, such as triglycerides.

Topical Compositions

The term "topical" refers to administration of an inventive composition at, or immediately beneath, the point of application. The phrase "topically applying" describes application onto one or more surfaces(s) including epithelial surfaces. Although topical administration, in contrast to transdermal administration, generally provides a local rather than a systemic effect, as used herein, unless otherwise stated or implied, the terms topical administration and transdermal administration are used interchangeably. For the purpose of this application, topical applications shall include mouthwashes and gargles.

Topical administration may also involve the use of transdermal administration such as transdermal patches or iontophoresis devices which are prepared according to techniques and procedures well known in the art. The terms "transdermal delivery system," "transdermal patch" or "patch" refer to an adhesive system placed on the skin to deliver a time released dose of a drug(s) by passage from the dosage form through the skin to be available for distribution via the systemic circulation. Transdermal patches are a well-accepted technology used to deliver a wide variety of pharmaceuticals, including, but not limited to, scopolamine for motion sickness, nitroglycerin for treatment of angina pectoris, clonidine for hypertension, estradiol for post-menopausal indications, and nicotine for smoking cessation.

Patches suitable for use in the present invention include, but are not limited to, (1) the matrix patch; (2) the reservoir patch; (3) the multi-laminate drug-in-adhesive patch; and (4) the monolithic drug-in-adhesive patch; Transdermal and Topical Drug Delivery Systems, pp. 249-297 (Tapash K. Ghosh et al. eds., 1997), hereby incorporated herein by reference. These patches are well known in the art and generally available commercially.

Carriers and Other Components

In some embodiments, the compositions of the present invention may be formulated with an excipient, vehicle or carrier selected from solvents, suspending agents, binding agents, fillers, lubricants, disintegrants, and wetting agents/surfactants/solubilizing agents. The terms "excipient", "vehicle", or "carrier" refer to substances that facilitate the use of, but do not deleteriously react with, the active compound(s) when mixed with it. The term "active" refers to the ingredient, component or constituent of the compositions of the present invention responsible for the intended therapeutic effect. Carriers must be of sufficiently high purity and of sufficiently low toxicity to render them suitable for administration to the subject being treated. The carrier can be inert, or it can possess pharmaceutical benefits.

The carrier can be liquid or solid and is selected with the planned manner of administration in mind to provide for the desired bulk, consistency, etc., when combined with an active and the other components of a given composition. Typical pharmaceutical carriers include, but are not limited to, binding agents (including, but not limited to, pregelatinized maize starch, polyvinylpyrrolidone or hydroxypropyl methylcellulose); fillers (including, but not limited to, lactose and other sugars, microcrystalline cellulose, pectin, gelatin, calcium sulfate, ethyl cellulose, polyacrylates or calcium hydrogen phosphate.); lubricants (including, but not limited to, magnesium stearate, talc, silica, sollidal silicon dioxide, stearic acid, metallic stearates, hydrogenated vegetable oils, corn starch, polyethylene glycols, sodium benzoate, sodium acetate); disintegrants (including, but not limited to, starch, sodium starch glycolate) and wetting agents (including, but not limited to, sodium lauryl sulfate). Additional suitable carriers for the compositions of the present invention include, but are not limited to, water, salt solutions, alcohol, vegetable oils, polyethylene glycols, gelatin, lactose, amylose, magnesium stearate, talc, silicic acid, viscous paraffin, perfume oil; fatty acid monoglycerides and diglycerides, petroethral fatty acid esters, hydroxymethylcellulose, polyvinylpyrrolidone, and the like. The pharmaceutical preparations can be sterilized and if desired, mixed with auxiliary agents, for example, lubricants, preservatives, stabilizers, wetting agents, emulsifiers, salts for influencing osmotic pressure, buffers, colorings, flavoring and/or aromatic substances and the like which do not deleteriously react with the active compounds.

The term "pharmaceutically acceptable carrier" as used herein refers to any substantially non-toxic carrier conventionally useful for administration of pharmaceuticals in which the active component will remain stable and bioavailable. In some embodiments, the pharmaceutically acceptable carrier of the compositions of the present invention include a release agent such as a sustained release or delayed release carrier. In such embodiments, the carrier can be any material capable of sustained or delayed release of the leptin peptide active ingredient to provide a more efficient administration, resulting in less frequent and/or decreased dosage of the active ingredient, ease of handling, and extended or delayed effects. Non-limiting examples of such carriers include liposomes, microsponges, microspheres, or microcapsules of natural and synthetic polymers and the like. Liposomes may be formed from a variety of phospholipids such as cholesterol, stearylamines or phosphatidylcholines.

In some embodiments, the compositions of the present invention can further include one or more compatible active ingredients aimed at providing the composition with another pharmaceutical effect in addition to that provided by a leptin composition, therapeutically active leptin, leptin mimic peptide or a derivative thereof. "Compatible" as used herein means that the active ingredients of such a composition are capable of being combined with each other in such a manner so that there is no interaction that would substantially reduce the efficacy of each active ingredient or the composition under ordinary use conditions. In another aspect of the present invention, the composition also may be administered serially or in combination with other compositions for treating diseases, conditions or disorders resulting from accumulation of amyloid peptides. For example, without limitation, such other compositions may include monoclonal antibodies (such as monoclonal anti-β-Amyloids and monoclonal anti-β-secretases); and anti-inflammatory compounds (including, but not limited to nonsteroidal anti-inflammatory drugs (NSAIDs), such as ibuprofen, indomethacin, and flurbiprofen). Anti-inflammatory compounds have been shown to direct Aβ-lowering properties in cell cultures as well as in transgenic models of AD-like amyloidosis.

The concentration of the active substance is selected so as to exert its therapeutic effect, but low enough to avoid significant side effects within the scope and sound judgment of the skilled artisan. The effective amount of the composition may vary with the age and physical condition of the biological subject being treated, the severity of the condition, the duration of the treatment, the nature of concurrent therapy, the specific compound, composition or other active ingredient employed, the particular carrier utilized, and like factors. Those of skill in the art can readily evaluate such factors and, based on this information, determine the particular effective concentration of a composition of the present invention to be used for an intended purpose. Additionally, in therapeutic applications of the present invention, compositions or medicants are administered to a patient suspected of, having, or already suffering from, such a disease, disorder or condition in an amount sufficient to cure, or at least partially arrest, the symptoms of the disease, disorder or condition, including its complications and intermediate pathological phenotypes in development of the disease, disorder or condition. In some methods, administration of the composition of the present invention reduces or eliminates cognitive impairment in patients that have not yet developed characteristic pathology of the disease, disorder or condition.

An amount adequate to accomplish therapeutic or prophylactic treatment is defined herein as a therapeutically-effective dose. In both prophylactic and therapeutic regimes, an amount of the compositions of the present invention is usually administered in several dosages until a sufficient beneficial response has been achieved. Typically, the response is monitored and repeated dosages are given if the response starts to wane. A skilled artisan can determine a pharmaceutically effective amount of the inventive compositions by determining the dose in a dosage unit (meaning unit of use) that elicits a given intensity of effect, hereinafter referred to as the "unit dose." The term "dose-intensity relationship" refers to the manner in which the intensity of effect in an individual recipient relates to dose. The intensity of effect generally designated is 50% of maximum intensity. The corresponding dose is called the 50% effective dose or individual ED50. The use of the term "individual" distinguishes the ED50 based on the intensity of effect as used herein from the median effective dose, also abbreviated ED50, determined from frequency of response data in a population. "Efficacy" as used herein refers to the property of the compositions of the present invention to achieve the desired response, and "maximum efficacy" refers to the maximum achievable effect. The amount of compounds in the compositions of the present invention which will be effective in the treatment of a particular disorder or condition will depend on the nature of the disorder or condition, and can be determined by standard clinical techniques. (See, for example, Goodman and Gilman's THE PHARMACOLOGICAL BASIS OF THERAPEUTICS, Joel G. Harman, Lee E. Limbird, Eds.; McGraw Hill, New York, 2001; THE PHYSICIAN'S DESK REFERENCE, Medical Economics Company, Inc., Oradell, N.J., 1995; and DRUG FACTS AND COMPARISONS, FACTS AND COMPARISONS, INC., St. Louis, Mo., 1993). The precise dose to be employed in the formulation will also depend on the route of administration, and the seriousness of the disease or disorder, and should be decided according to the judgment of the practitioner and each patient's circumstances. Various administration patterns will be apparent to those skilled in the art.

The dosage ranges for the administration of the compositions of the present invention are those large enough to produce the desired therapeutic effect. Preferably, the therapeutically effective amount of the compositions of the present invention is administered one or more times per day on a regular basis. A typical dose administered to a subject is between about 0.01 mg of the composition per kg (of body weight) per day and about 0.5 mg of the composition per kg (of body weight) per day. For example, without limitation, the minimum dose of the composition is contemplated as about 0.01 mg/kg/day, about 0.025 mg/kg/day, about 0.05 mg/kg/day, about 0.075 mg/kg/day, about 0.08 mg/kg/day, about 0.1 mg/kg/day, about 0.125 mg/kg/day, about 0.15 mg/kg/day, about 0.175 mg/kg/day, about 0.2 mg/kg/day, about 0.225 mg/kg/day, about 0.25 mg/kg/day, about 0.275 mg/kg/day, about 0.3 mg/kg/day, about 0.325 mg/kg/day, about 0.35 mg/kg/day, about 0.375 mg/kg/day, about 0.4 mg/kg/day, about 0.45 mg/kg/day, about 0.475 mg/kg/day, or about 0.5 mg/kg/day and the maximum dose is contemplated as about 0.5 mg/kg/day, about 0.475 mg/kg/day, about 0.45 mg/kg/day, about 0.4 mg/kg/day, about 0.375 mg/kg/day, about 0.35 mg/kg/day, about 0.325 mg/kg/day, about 0.3 mg/kg/day, about 0.275 mg/kg/day, about 0.25 mg/kg/day, bout 0.225 mg/kg/day, about 0.2 mg/kg/day, about 0.175 mg/kg/day, about 0.15 mg/kg/day, about 0.125 mg/kg/day, about 0.1 mg/kg/day, about 0.08 mg/kg/day, about 0.075 mg/kg/day, about 0.05 mg/kg/day, about 0.025 mg/kg/day, or about 0.01 mg/kg/day. In some embodiments of the invention in humans, the dose may be about 0.01 mg to about 0.3 mg of the composition per kg (of body weight) per day, and in other embodiments in humans, between 0.01 and 0.08 mg of the composition per kg (of body weight) per day.

Additional compositions of the present invention can be prepared readily using technology is known in the art, such as that which is described in Remington's Pharmaceutical Sciences, 18th or 19th editions, published by the Mack Publishing Company of Easton, Pa., which is incorporated herein by reference.

Administration

According to another embodiment of the method, the method comprises the step of implanting surgically or injecting a leptin composition gel, leptin composition slow-release solid or leptin composition semisolid into the patient to deliver drug substance at the site of interest. Because the leptin composition gel, leptin composition slow-release solid or leptin composition semisolid agent is delivered specifically (locally) to the site, the dosage required to treat the progressive cognitive disorder will be appropriate, to reduce, prevent or circumvent the main side effect that prevents the administration of higher systemic doses, e.g., toxicity. It is desired to deliver efficacious amounts of this agent to a specific site (without unwanted side effects).

Controlled Release Systems

The therapeutic agent(s), including, but not limited to, a leptin composition, may be contained in controlled release systems. In order to prolong the effect of a drug, it often is desirable to slow the absorption of the drug from subcutaneous, intrathecal, or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form.

The term "controlled release" is intended to refer to any drug-containing formulation in which the manner and profile of drug release from the formulation are controlled. This refers to immediate as well as non-immediate release formulations, with non-immediate release formulations including, but not limited to, sustained release and delayed release formulations. The term "sustained release" (also referred to as "extended release") is used herein in its conventional sense to refer to a drug formulation that provides for gradual release of a drug over an extended period of time, and that preferably, although not necessarily, results in substantially constant blood levels of a drug over an extended time period. Alternatively, delayed absorption of a parenterally administered drug form is accomplished by dissolving or suspending the drug in an oil vehicle. The term "delayed release" is used herein in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. The term "long-term" release, as used herein, means that the implant is constructed and arranged to deliver therapeutic levels of the active ingredient for at least 7 days, and preferably about 30 to about 60 days. Long-term sustained release implants are well-known to those of ordinary skill in the art and include some of the release systems described above.

According to another embodiment, the pharmaceutically acceptable carrier of the present invention includes a sustained release or delayed release carrier. The carrier can be any material capable of sustained or delayed release of the compound to provide a more efficient administration resulting in less frequent and/or decreased dosage of the compound, ease of handling, and extended or delayed effects on epithelial-related conditions.

According to another aspect, the described invention provides a method of improving resilience of cognitive function in a subject in need thereof, the method comprising the step of (a) administering to the subject a composition comprising: (i) a cognitive function-enhancing amount of a leptin composition, and (ii) a pharmaceutically acceptable carrier. According to one embodiment, the leptin composition comprises at least one of a leptin, a leptin mimic, a leptin derivative, an AMP-dependent protein kinase activator, a leptin agonist, a leptin blocker, a mimic of a leptin blocker, a leptin antagonist, an AMP-dependent protein kinase inhibitor; or pharmaceutically acceptable salts thereof. According to another embodiment, the leptin composition further comprises a second therapeutic agent. According to another embodiment, the second therapeutic agent is an antibiotic. According to another embodiment, the second therapeutic agent is an anti-fungal agent. According to another embodiment, the second therapeutic agent is an anti-viral agent. According to another embodiment, the second therapeutic agent is an anti-protozoal agent. According to another embodiment, the second therapeutic agent is a steroidal anti-inflammatory agent. According to another embodiment, the second therapeutic agent is a non-steroidal anti-inflammatory agent. According to another embodiment, the second therapeutic agent is an anti-oxidant. According to another embodiment, the second therapeutic agent is a hormone. According to another embodiment, the second therapeutic agent is a vitamin. According to another embodiment, the second therapeutic agent is an anti-histamine agent. According to another embodiment, the second therapeutic agent is a chemotherapetic agent.

Those skilled in the art will recognize that initial indications of the appropriate therapeutic dosage of the compositions of the invention can be determined in in vitro and in vivo animal model systems, and in human clinical trials. One of skill in the art would know to use animal studies and human experience to identify a dosage that can safely be administered without generating toxicity or other side effects. For acute treatment, it is preferred that the therapeutic dosage be close to the maximum tolerated dose. For chronic preventive use, lower dosages may be desirable because of concerns about long term effects.

The effectiveness of the compositions and methods of the present invention can be assayed by a variety of protocols. The effects of increasing cognitive function in a human subject can be determined by methods routine to those skilled in the art including, but not limited to, both paper and pencil, and computer tests. One of skill in the art can also directly measure amyloid peptide accumulation levels, neurofibrillary tangle formation and neurodegeneration in animal models. Furthermore, amyloid peptide may be measured in a sample of a subject's cerebrospinal fluid (CSF) obtained by spinal tap. One measure of accumulation of an amyloid peptide is an increase in levels circulating in the blood of a subject. Such levels may be measured by Sandwich Enzyme-linked-Immunoabsorbent-Assays (ELISAs), using a pair of antibodies, one for capture and the other for detection. These methods are well known by those of ordinary skill in the art.

Unless defined otherwise, all technical and scientific terms used herein have the same meaning as commonly understood by one of ordinary skill in the art to which this invention belongs. Although any methods and materials similar or equivalent to those described herein also can be used in the practice or testing of the present invention, the preferred methods and materials are now described. All publications mentioned herein are incorporated herein by reference to disclose and describe the methods and/or materials in connection with which the publications are cited.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto. Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

It must be noted that as used herein and in the appended claims, the singular forms "a", "and", and "the" include plural references unless the context clearly dictates otherwise. All technical and scientific terms used herein have the same meaning.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The present invention may be embodied in other specific forms without departing from the spirit or essential attributes thereof and, accordingly, reference should be made to the appended claims, rather than to the foregoing specification, as indicating the scope of the invention.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Reagents and Antibodies

Minimum essential medium (MEM) was purchased from ATCC (Manassas, Va.). Neurobasal medium, B27 supplement and L-glutamine were purchased from Gibco (Carlsbad, Calif.). Trypsin-EDTA and penicillin-streptomycin-amphotericin solution were purchased from MP Biomedicals (Solon, Ohio). Fetal bovine serum (FBS), all-trans retinoic acid (RA), also known as ATRA, human recombinant leptin and human recombinant insulin were purchased from Sigma-Aldrich (St. Louis, Mo.). 5-Aminoimidazole-4-carboxyamide ribonucleoside (AICAR), a drug widely used to activate AMP-dependent protein kinase (AMPK) experimentally, was purchased from Cell Signaling Technology (Danvers, Mass.). Upon activation, AMPK is known to promote lipolysis and to inhibit lipogenesis.

Rabbit anti-AMPKα (pThr$^{172}$), Rabbit anti-AMPKα (total) and tau (pSer$^{396}$) mouse mAb were purchased from Cell Signaling Technology. Tau mouse mAb (clone 5E2) for detection of total tau was purchased from Upstate Cell Signaling Solutions (Lake Placid, N.Y.). PHF-tau mouse mAb (clone AT8) was purchased from Pierce Biotechnology (Rockford, Ill.). PHF-1 mouse mAb was a gift from Dr. Peter Davies, Albert Einstein College of Medicine (Bronx, N.Y.). Rabbit anti-leptin receptor (OB-R) and α-tubulin mouse mAb were purchased from Affinity BioReagents (Golden, Colo.). Insulin receptor (β-subunit) mAb was purchased from Millipore (Billerica, Mass.).

Culture of Cell Lines

The human neuroblastoma, SH-SY5Y, and embryonal carcinoma, NTera-2 (NT2), cell lines were purchased from American Type Culture Collection (ATCC). Cell culture was performed according to manufacturer's specific guidelines. Briefly, SY5Y and NT2 cells were propagated on 25 cm$^2$ tissue-culture flasks (Corning; Corning, N.Y.) in minimum essential medium (MEM) (Eagle) containing 10% fetal bovine serum (FBS) until 80-90% confluence was established. SY5Y and NT2 cells were detached from the flask by 0.1% trypsin-EDTA and gentle scraping, respectively, and sub-cultured at a ratio of 1:5.

Neuronal Induction

To induce neuronal differentiation, 1×10$^6$ SY5Y or NT2 cells were seeded in 25 or 75 cm$^2$ tissue-culture flasks, respectively. Cells were grown in neuronal induction medium (NIM), which consisted of MEM containing 5% FBS supplemented with 10 μM RA. SY5Y were grown in NIM for 6 days, and switched to serum-free NIM prior to treatment and harvesting on day 7. To induce neuronal differentiation of NT2 cells was based on a previously described protocol [P. W. Andrews, Retinoic acid induces neuronal differentiation of a cloned human embryonal carcinoma cell line in vitro, Dev. Biol. 103 (1984) 285-293, which is incorporated herein by reference]. Briefly, NT2 cells were cultured in NIM for 5 weeks, with 50% NIM replacement every 3 days. Differentiated NT2 cells (NT2N) were switched to serum-free NIM on the day prior to treatment and harvesting.

Culture of Rat Primary Neurons

Primary rat cortical neurons were purchased from BrainBits LLC (Springfield, Ill.), and cultured as per manufacturer's instructions. Briefly, tissues were dispersed and supernatant was transferred to a new tube and centrifuged for 1 min at 1100 rpm. The neurons then were seeded in 6-well plates coated with poly-D-lysine (BD Biosciences; San Jose, Calif.) and grown in Neurobasal medium supplemented with B27 supplement (Invitrogen) and 0.5 mM L-glutamine. Medium was changed after 4 days, and at 7 days in culture the neurons were treated and harvested.

Protein Extraction and Western Blotting

Western blot (or immunoblot) analysis is a method to detect a specific protein in a given sample of a tissue homogenate or extract generally uses SDS-gel electrophoresis to separate typically denatured proteins by the molecular weight of the polypeptide. Proteins are then transferred to a membrane (typically nitrocellulose or PVDF) where they are detected using antibodies specific to the target protein.

Following treatment with leptin, insulin and/or AICAR, SY5Y, NT2N and rat cortical neurons were harvested by scraping. Cell pellets were washed twice in ice-cold 1×PBS (phosphate buffered saline) (pH 7.4), resuspended in protease and phosphotase inhibitor-supplemented 1×RIPA lysis/extraction buffer consisting of 25 mM Tris-HCl, pH 7.6, 150 mM NaCl, 1% NP-40, 1% sodium deoxycholate and 0.1% SDS (Pierce), and then subjected to freeze/thaw cycles in a dry ice/ethanol bath. Cell-free, whole cell lysates were obtained and total protein was determined with the Coomassie (Bradford) Protein Assay Kit (Pierce). Whole cell extracts (25 μg) were analyzed by western blots using 10% SDS-PAGE pre-cast gels (Lonza; Rockland, Me.), and the separated proteins were transferred onto polyvinylidene difluoride membranes (Millipore). Membranes were incubated overnight at 4° C. with primary antibodies and then detected the following day by 2 hr incubation with HRP-conjugated IgG. All primary antibodies, except tau-pSer$^{396}$ (1:500), total tau (1:500) and PHF-tau AT8 (1:200), and secondary antibodies were used at final dilutions of 1:1,000 and 1:10,000, respectively. HRP was developed with SuperSignal West Pico Chemiluminescent Substrate (Pierce), and imaged using a BioRad (Hercules, Calif.) ChemiDoc XRS System. The membranes were stripped with Restore PLUS Western Blot Stripping Buffer (Pierce) for reprobing with other antibodies. Blocking buffer consisted of 5% milk in 0.1% Tween in TBS (Tris buffered saline).

Statistical Analysis

Statistical data analyses were performed with analysis of variance and Tukey-Kramer multiple comparisons test. Densitometric analyses were performed using the UN-SCAN-IT gel 6.1 software (Silk Scientific; Orem, Utah). $p < 0.05$ was considered statistically significant.

Example 1

Leptin and Tau Phosphorylation in RA-Induced SY5Y Cells

RA induction of the human neuroblastoma cell line, SY5Y, has been reported to induce hyperphosphorylation of tau at AD-related sites. We therefore utilized SY5Y cells induced with retinoic acid (RA-SY5Y) for 7 days as our primary in vitro model to investigate the effects of leptin and other treatments on tau phosphorylation.

The first set of studies examined expression of the leptin receptor (OB-R) in RA-SY5Y cells treated with 400 ng/ml leptin or placebo. Both treated and placebo cells were found to express relatively high levels of OB-R (FIG. 1A). We next determined whether leptin had an effect on tau phosphorylation. Cells were treated for a range of time periods with 400 ng/ml leptin or placebo, and phosphorylation of tau at Ser$^{396}$, a site within the microtubule-binding region of tau, was measured (FIG. 1B and FIG. 1C). Significant ($p < 0.05$) decreases in tau (Ser$^{396}$) phosphorylation were observed in cells treated with leptin for 1 hour, 2 hours or 4 hours compared to placebo (FIG. 1C; far right bars). No change in tau (Ser$^{396}$) phosphorylation was observed in cells treated with leptin for 24 hours compared to 4 hours (data not shown).

To determine the dose-response relationship between leptin and tau Ser$^{396}$ phosphorylation, RA-SY5Y cells were treated with leptin for 4 hours at a range of concentrations (FIG. 1D and FIG. 1E). We observed a significant ($p < 0.05$) decrease in tau (Ser$^{396}$) phosphorylation in cells treated with 100 ng/ml leptin (FIG. 1E; second bar from left). Decreasing tau (Ser$^{396}$) phosphorylation was observed up to a concentration of 1600 ng/ml leptin (second bar from right), which produced the maximal effect. Estimation of the 50% inhibitory concentration (IC$_{50}$) of leptin for tau (Ser$^{396}$) phosphorylation provided a value of 750 ng/ml, or 46.9 nM.

Example 2

Insulin and Tau Phosphorylation in RA-Induced SY5Y Cells

We tested the effect of insulin treatment on tau (Ser$^{396}$) phosphorylation in RA-SY5Y cells and compared it to that of leptin.

The first set of studies examined expression of the insulin receptor in RA-SY5Y cells treated with 10 μM insulin or placebo. Both insulin and placebo-treated cells were found to express high levels of insulin receptor (FIG. 2A). We next determined the effect of insulin on tau phosphorylation. Cells were treated for a range of time periods with 10 μM insulin or placebo, and phosphorylation of tau (Ser$^{396}$) was measured (FIG. 2B and FIG. 2C). Significant ($p < 0.05$) decreases in tau (Ser$^{396}$) phosphorylation were observed in cells treated with insulin for 2 hours or 4 hours compared to placebo-treated cells (FIG. 2C; far right bars). No change in tau (Ser$^{396}$) phosphorylation was observed in cells treated with insulin for 24 hours compared to 4 hours (data not shown).

As in the leptin studies (FIG. 1D and FIG. 1E), a dose-response curve for insulin on tau (Ser$^{396}$) phosphorylation was established in RA-SY5Y cells (FIG. 2D and FIG. 2E). We observed a significant ($p < 0.05$) decrease in tau (Ser$^{396}$) phosphorylation in cells treated with 10 μM insulin (FIG. 2E; third bar from right). Further, maximum decrease of tau (Ser$^{396}$) phosphorylation was observed at a concentration of 20 μM insulin (second bar from right). Estimation of the 50% inhibitory concentration (IC$_{50}$) of insulin for tau (Ser$^{396}$) phosphorylation provided a value of 13.8 μM.

Figure 2:
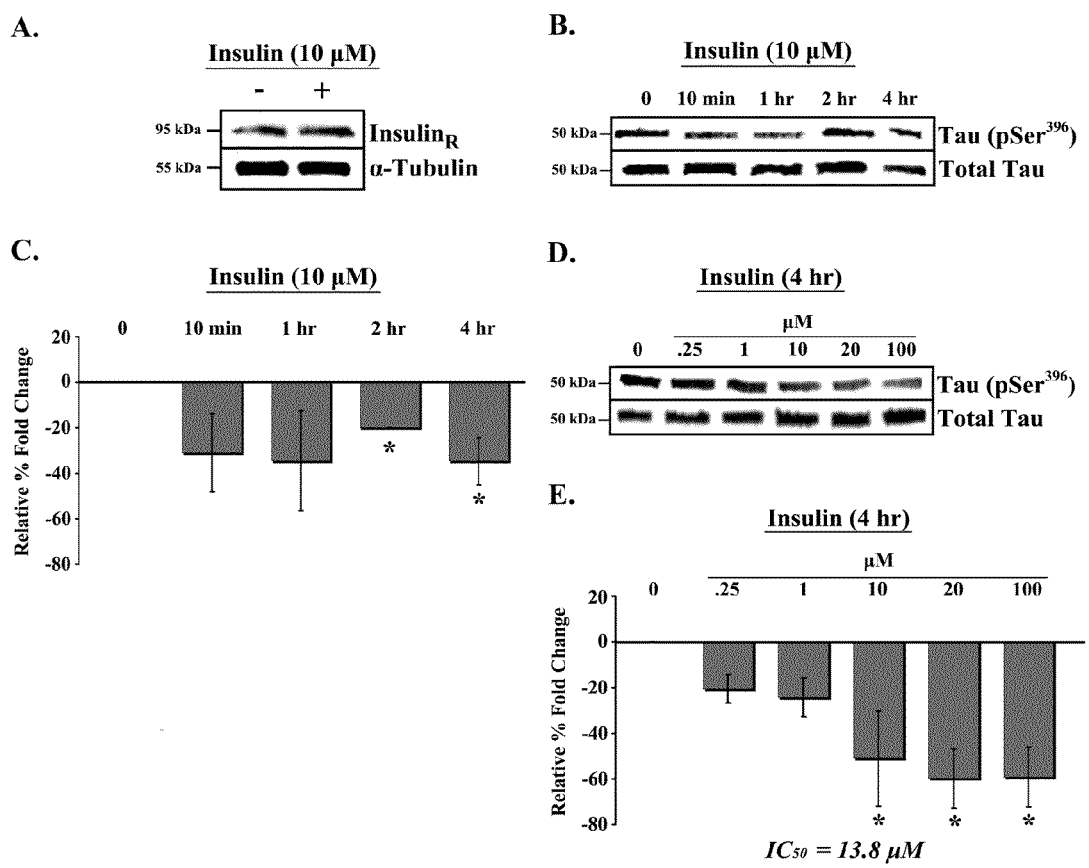
FIG. 2 shows time- and dose-dependent dephosphorylation of tau by insulin in RA-SY5Y. A. RA-SY5Y were treated with insulin (10 μM) for 4 hrs, or non-treated (placebo). Whole cell extracts were prepared and analyzed by western blot with anti-insulin receptor (β-subunit). Membranes were stripped and re-probed with anti-α-tubulin for normalization. Representative blot is shown, n=3. B. Whole cell extracts from cells treated for various times with insulin (10 μM), or placebo, were prepared and analyzed by western blot with anti-tau (pSer$^{396}$). Membranes were stripped and re-probed with anti-tau (total) for normalization. Representative blot is shown, n=3. C. Normalized band densities from B were analyzed by densitometry. Results are presented as the mean±SD percent fold change, relative to placebo-treated samples, which were arbitrarily assigned a value of 0. D. Induced cells were treated with various concentrations of insulin for 4 hrs, or placebo. Experiments were then performed as in B. E. Normalized band densities from D were analyzed as in C. $IC_{50}$ represents the insulin concentration at which tau (pSer$^{396}$) phosphorylation is decreased by 50 percent. *p<0.05 vs. non-treated.

Summary:

The effect of leptin on the level of tau phosphorylation at sites known to be hyperphosphorylated in AD was studied. RA-induced, human SY5Y express hyperphosphorylated tau, and thus were utilized in our treatment model. Since insulin reduces the level of phosphorylated tau in both in vitro and in vivo models, our studies began by comparing the efficacy of leptin to insulin (FIGS. 1 and 2). Leptin was found to reduce tau phosphorylation by 50% at a concentration (FIG. 1; $IC_{50}$=46.9 nM) that was 300-fold less than that of insulin (FIG. 2; $IC_{50}$=13.8 µM).

Example 3

Combined Leptin and Insulin Treatment and Tau Phosphorylation

RA-SY5Y cells were treated for 4 hours with sub-optimal or maximum effect doses, either in combination or alone, of leptin and/or insulin, and tau ($Ser^{396}$) phosphorylation was measured (FIG. 3A and FIG. 3B). A significant (p<0.05) decrease in phosphorylation was observed in cells treated with sub-optimal combinations of leptin (100 ng/ml) and insulin (1 µM) compared to either treatment alone (FIG. 3B; first, third and fifth bars from left). Co-treatment with maximum effect doses of leptin (1600 ng/ml) and insulin (20 µM) produced the most significant (p<0.01) decrease in phosphorylation (first bar from right) compared to placebo-treated. Co-treatment with maximum effect doses of leptin and insulin did not produce a significant (p>0.05) reduction in tau ($Ser^{396}$) phosphorylation compared to either treatment alone.

Figure 3:
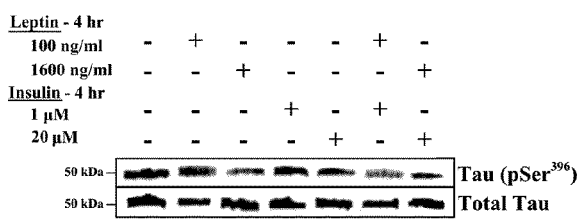
FIG. 3 shows that combined treatment of leptin and insulin produces a greater dephosphorylation of tau than either treatment alone. A. RA-SY5Y were treated with low or high concentrations of leptin (100 or 1600 ng/ml) and/or insulin (1 or 20 μM) for 4 hrs, or non-treated (placebo). Whole cell extracts were prepared and analyzed by western blot with anti-tau (pSer$^{396}$). Membranes were stripped and re-probed with anti-tau (total) for normalization. Representative blot is shown, n=3. B. Normalized band densities from A were analyzed by densitometry. Results are presented as the mean±SD percent fold change, relative to placebo-treated samples, which were arbitrarily assigned a value of 0. C. Cells were treated for 4 hrs with leptin (1600 ng/ml) and insulin (20 μM), or placebo. To re-induce tau phosphorylation, cold PBS was added to the post-treated cells for 10 min, 1 hr or not at all. Experiments were then carried out as in A. D. Normalized band densities from C were analyzed as in B. *p<0.05 vs. group. **p<0.01 vs. group
Figure 3:
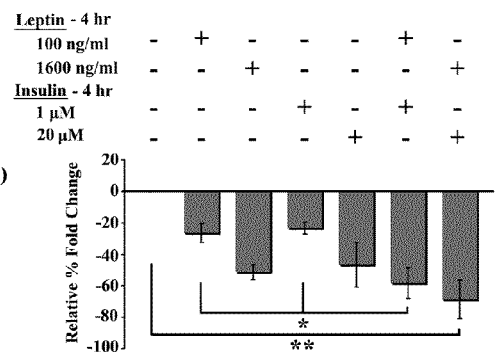
Figure 3:
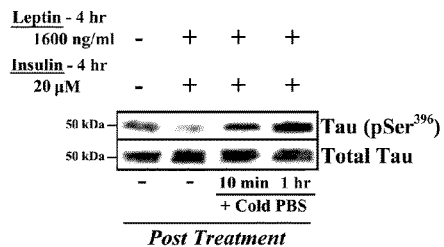
Figure 3:
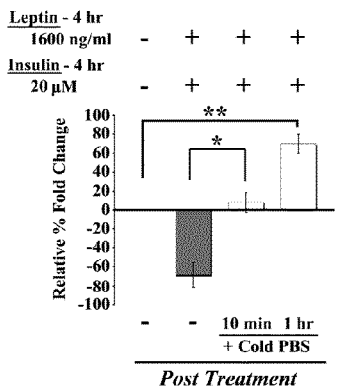

Summary:

The combined treatment with sub-optimal doses of leptin (100 ng/ml) and insulin (1 µM) produced a significant decrease in tau phosphorylation compared to either treatment alone (FIG. 3). This result demonstrates the potential benefits of a combinatorial treatment for AD, as leptin and insulin may produce an additive effect.

Example 4

Reversibility of Leptin- and Insulin-Induced Dephosphorylation

Tau phosphorylation has been reported to increase with cold temperature stress in animals. We thus utilized a similar approach to determine whether the leptin- and insulin-induced dephosphorylation of tau at $Ser^{396}$ was reversible. RA-SY5Y were co-treated with leptin (1600 ng/ml) and insulin (20 µM) for 4 hours, or placebo. At the end of the treatment period, cells were either harvested or post-treated with ice-cold PBS (pH 7.4) for 10 minutes or 1 hour (FIG. 3C and FIG. 3D). Cells post-treated with cold PBS for 10 minutes showed a significant (p<0.05) increase in tau phosphorylation compared to co-treatment alone (FIG. 3D; first and second bars from left). Cells post-treated with cold PBS for 1 hour showed significant (p<0.01) hyperphosphorylation of tau compared to cells with no treatment at all (first bar from right). These results suggest that the effects of leptin and insulin on dephosphorylation of tau are reversible. The results also demonstrate antibody specificity regarding the phosphorylated form of tau.

Example 5.1

Leptin, Insulin and Tau Phosphorylation at Other AD-Related Sites

To evaluate if the observed effects of leptin and insulin on tau phosphorylation at $Ser^{396}$ (FIG. 1 and FIG. 2) is consistent with other AD-related sites, antibodies raised against tau epitopes known to be phosphorylated in paired helical filament (PHF) tau were utilized. PHFs are a principal component of NFT pathology, which results from tau hyperphosphorylation and subsequent microtubule destabilization and oligomer formation. Tau phosphorylated at $Ser^{396/404}$ and $Ser^{202}/Thr^{205}$ is recognized by PHF-1 (mouse) and AT8 (mouse) antibodies, respectively.

RA-SY5Y cells were treated with leptin and/or insulin as in FIG. 3A and FIG. 3B, and phosphorylation of specific tau sites was measured (Table 1).

TABLE 1

Relative tau phosphorylation in treated neuronal cultures

| Cell Type | PhosphoSite | Non-Treated | Leptin 100 ng/ml | Leptin 800 ng/ml | Leptin 1600 ng/ml | Insulin 1 µM | Insulin 20 µM | Leptin 100 ng/ml + Insulin 1 µM | Leptin 1600 ng/ml + Insulin 20 µM |
|---|---|---|---|---|---|---|---|---|---|
| RA-SY5Y | $pSer^{396}$ | 0 | −26 ± 6* | ND | −51 ± 5* | −23 ± 4* | −47 ± 14* | −58 ± 10* | −69 ± 12* |
|  | PHF-1 | 0 | −20 ± 19 | ND | −67 ± 4* | −37 ± 11* | −80 ± 7* | −72 ± 3* | −84 ± 6* |
|  | AT8 | 0 | −10 ± 5 | ND | −60 ± 19* | −40 ± 13* | −57 ± 14* | −61 ± 17* | −66 ± 21* |
| NT2N | $pSer^{396}$ | 0 | −27 ± 6* | ND | −27 ± 5* | −23 ± 6* | −53 ± 10* | −42 ± 7* | −48 ± 1* |
| Rat 1° Neuron | PHF-1 | 0 | ND | −75 ± 18* | ND | ND | ND | ND | ND |
|  | AT8 | 0 | ND | 5 ± 23 | ND | ND | ND | ND | ND |

Briefly, RA-induced SY5Y and NT2N were treated with low and high concentrations of leptin (100 ng/ml or 1600 ng/ml) and/or insulin (1 µM or 20 µM) for 4 hours, or non-treated (placebo). Primary rat cortical neurons were treated with leptin for 24 hours or placebo. Whole cell extracts were prepared and analyzed by Western blot with phosphorylated tau-specific antibodies ($pSer^{396}$, PHF-1 or AT8). Membranes were stripped and re-probed with anti-tau (total) for normalization. Normalized band densities were analyzed by densitometry and results are presented as the mean±SD percent fold change, relative to non-treated samples, which were arbitrarily assigned a value of 0. (ND—Not Determined). (*p<0.05 vs non-treated).

Leptin and/or insulin treatment was observed to have a similar effect on the phosphorylation of tau as detected by PHF-1 and AT8 antibodies (Table 1). The only observable difference was that leptin at 100 ng/ml was unable to induce a significant (p>0.05) decrease in phosphorylation of tau, compared to that observed with $pSer^{396}$ antibody. These findings demonstrate that both leptin and insulin treatment of RA-SY5Y cells reduces phosphorylation of at least two separate AD-related tau sites.

Example 5.2

Leptin, Insulin and Tau Phosphorylation in Other Neuronal Cells

We next determined whether the effect of leptin and/or insulin on tau phosphorylation was unique to RA-SY5Y cells or consistent with other neuronal cells. For this approach, we utilized human NT2 cells, which undergo neuronal differentiation with RA treatment (NT2N), as well as rat primary cortical neurons.

NT2N cells were treated with leptin and/or insulin as in FIG. 3A and FIG. 3B, and tau phosphorylation at $Ser^{396}$ was measured (Table 1). Insulin and combined insulin/leptin treatment were observed to have a similar effect to that observed with RA-SY5Y cells (Table 1).

For the rat primary neurons, we determined the effect of 24 hour leptin treatment on phosphorylation of tau, as detected by PHF-1 and AT8 antibodies (Table 1). A mid-range dose of leptin (800 ng/ml) was chosen, since this concentration produced a 50% decrease ($ID_{50}$) in tau phosphorylation within RA-SY5Y (FIG. 1). Leptin produced a significant ($p<0.05$) decrease in tau phosphorylation, as detected by PHF-1 antibody compared to placebo-treated cells (Table 1). However, the leptin-induced decrease in tau phosphorylation was not detected by the AT8 antibody (Table 1).

In summary, leptin induces a reduction in phosphorylation of tau at $Ser^{396/404}$ (as detected by PHF-1 antibody) in several neuronal cells. Further, it induces a reduction of tau phosphorylation at $Ser^{202}/Thr^{205}$ (as detected by AT8 antibody) in most but not all neuronal cell types tested.

Summary:

Tau phosphorylation in human NT2N cells and rat primary cortical neurons (Table 1) was examined to demonstrate the effects of leptin were consistent with other neuronal systems. Similar results were observed as in RA-SY5Y except that leptin did not significantly change phosphorylation of $Ser^{202}/Thr^{205}$ (AT8 mouse mAb) in rat cortical neurons. Without being limited by theory, this result may be related to the antibodies' species specificity.]

Example 6

AMPK Signaling and Tau Phosphorylation in RA-SY5Y Cells

The energy homeostasis enzyme AMP-activated protein kinase (AMPK) was directly stimulated with the cell-permeable activator, AICAR to study the influence of leptin and insulin in modulating tau phosphorylation.

Figure 4:
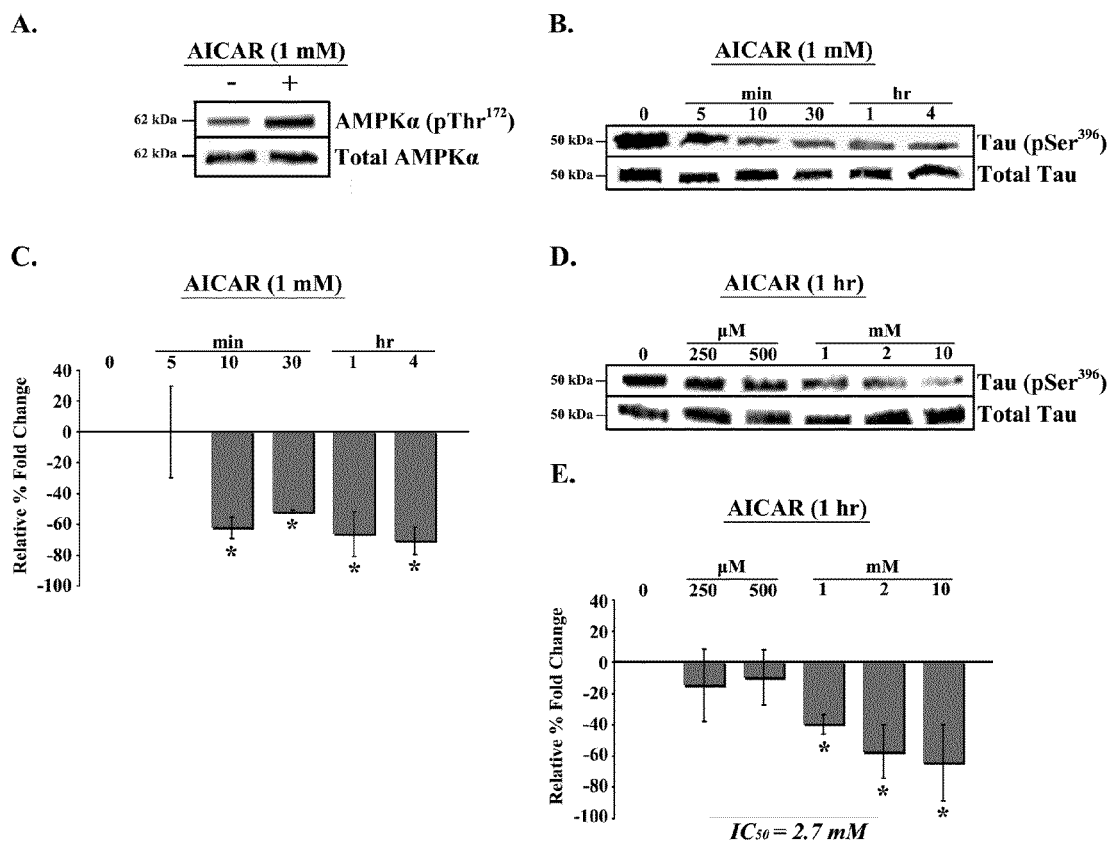
FIG. 4 shows dephosphorylation of tau by 5'-AMP-activated protein kinase (AMPK) activation in RA-SY5Y. A. Induced cells were treated with aminoimidazole carboxamide ribonucleotide which acts as an AMP-activated protein kinase agonist (AICAR) (1 mM) for 1 hr, or non-treated (placebo). Whole cell extracts were prepared and analyzed by western blot with AMPKα (pThr$^{172}$). Membranes were stripped and re-probed with anti-α-AMPKα (total) for normalization. Representative blot is shown, n=3. B. Whole cell extracts from cells treated for various times with AICAR (1 mM), or placebo, were prepared and analyzed by western blot with anti-tau (pSer$^{396}$). Membranes were stripped and re-probed with anti-tau (total) for normalization. Representative blot is shown, n=3. C. Normalized band densities from B were analyzed by densitometry. Results are presented as the mean±SD percent fold change, relative to placebo-treated samples, which were arbitrarily assigned a value of 0. D. Induced cells were treated with various concentrations of AICAR for 1 hr, or placebo. Experiments were then performed as in B. E.

AICAR treatment produced a large increase in $pThr^{172}$ AMPKα band density (FIG. 4A, top row), thus demonstrating efficient activation of AMPKα. We next determined the effect of AICAR on tau phosphorylation. RA-SY5Y were treated for various amounts of time with 1 mM AICAR or placebo-treated (FIG. 4B and FIG. 4C). Significant ($p<0.05$) decreases in $Ser^{396}$ phosphorylation were observed in cells treated with AICAR from 10 minutes to 4 hours, compared to placebo (FIG. 4C; gray bars).

RA-SY5Y were treated with AICAR for 1 hour at a range of concentrations, to establish a dose-response relationship (FIG. 4D and FIG. 4E). We observed a significant ($p<0.05$) decrease in $Ser^{396}$ phosphorylation in cells treated with 1 mM AICAR (FIG. 4E; third bar from right). Decreasing $Ser^{396}$ phosphorylation was observed up to a concentration of 2 mM AICAR (second bar from right), which produced the maximal effect. Estimation of the 50% inhibitory concentration ($IC_{50}$) of AICAR for tau ($Ser^{396}$) phosphorylation provided a value of 2.7 mM.

In summary, the observed results suggest that activation of AMPKα, by either leptin or insulin, could produce similar effects on tau phosphorylation at AD-related sites.

The point of convergence of the post-receptor signaling pathways in tau phosphorylation, was investigated. The energy homeostasis enzyme AMPK (FIG. 4) is known to be activated by insulin and leptin and is also known to interact with glycogen synthase kinase-3β (GSK-3β). Activation of AMPK with AICAR produced significant changes in tau phosphorylation within 10 minutes. These findings suggest that AMPK may provide a novel therapeutic target for reducing AD-related tau phosphorylation. We demonstrated that activation of AMPK mimics the leptin/insulin effect.

Example 7

Clinical Trials

The clinical development of leptin in humans is investigated. A pilot trial, [placebo-controlled double blinded] involving three groups of equal number of patients, diagnosed with early-stage Alzheimer's disease, receive by subcutaneous injections 0 mg (placebo), 5 mg, or 10 mg of leptin once daily for 16 weeks. CSF and serum samples are obtained in the beginning, during and at the end of the trial and Ab40, Ab42 and phosphor-tau are measured. Patients also receive neuropsychological evaluations at the beginning and at the end of the trial. This trial validates the preclinical findings and demonstrates leptin's value in selectively targeting both pathologies of AD.

The clinical trial data, taken with the preclinical data demonstrates that leptin ameliorates both Aβ and tau-related pathologies. Together with leptin's pharmacological profile these data support its use as a novel therapeutic for Alzheimer's disease.

Example 8

RA-Induced SY5Y and NT2N Treated with Leptin or Insulin

RA-induced SY5Y and NT2N were treated with low or high concentrations of leptin (100 ng/ml or 1600 ng/ml, respectively) and/or insulin (1 μM or 20 μM, respectively) for 4 hours, or non-treated (placebo) (Table 1). Primary rat cortical neurons were treated with leptin for 24 hours or placebo. Whole cell extracts were prepared and analyzed by western blot with phosphorylated tau-specific antibodies ($pSer^{396}$, PHF-1 or AT8). Membranes were stripped and re-probed with anti-tau (total) for normalization. Normalized band densities were analyzed by densitometry and results are presented as the mean±SD percent fold change, relative to non-treated samples, which were arbitrarily assigned a value of 0. (ND—Not Determined). *$p<0.05$ vs. non-treated.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed is:

1. A method for treating a neurodegenerative disorder characterized by accumulation of neurofibrillary tangles resulted from hyperphosphorylation of tau in brain, the method comprising administering to the subject in need thereof a composition comprising:
   (i). a therapeutically effective amount of a leptin composition, or a pharmaceutically acceptable salt thereof, wherein the therapeutically effective amount is effective to decrease the amount of hyperphosphorylated tau in brain, relative to the amount of hyperphosphorylated tau observed in a subject treated with placebo; and
   (ii). a pharmaceutically acceptable carrier, wherein the neurodegenerative disorder is Alzheimer's disease.

2. The method according to claim 1, wherein the therapeutically effective amount is an amount from about 0.01 mg/kg body weight to about 100 mg/kg body weight.

3. The method according to claim 1, wherein the composition further comprises a second therapeutic agent.

4. The method according to claim 3, wherein the second therapeutic agent is at least one therapeutic agent selected from the group consisting of an antibiotic, an anti-fungal agent, an antiviral agent, an anti-protozoal agent, an anti-inflammatory agent, an anti-oxidant, a hormone, a vitamin, an antihistamine agent, and a chemotherapeutic agent.

5. The method of claim 1, wherein the therapeutically effective amount of the leptin composition is effective to enhance the subject's cognitive function, mental processes of perception, memory, judgment or reasoning, to stabilize mental state, or to decelerate deterioration of mental function.

6. The method according to claim 5, wherein the leptin composition further comprises a second therapeutic agent.

7. The method according to claim 6, wherein the second therapeutic agent is at least one therapeutic agent selected from the group consisting of an antibiotic, an anti-fungal agent, an antiviral agent, an anti-protozoal agent, an anti-inflammatory agent, an anti-oxidant, a hormone, a vitamin, an antihistamine agent, and a chemotherapeutic agent.

8. The method according to claim 4, wherein the anti-inflammatory agent is a steroidal anti-inflammatory agent.

9. The method according to claim 4, wherein the anti-inflammatory agent is a non-steroidal anti-inflammatory agent.

10. The method according to claim 7, wherein the anti-inflammatory agent is a steroidal anti-inflammatory agent.

11. The method according to claim 7, wherein the anti-inflammatory agent is a non-steroidal anti-inflammatory agent.

* * * * *